US 9,597,440 B2

(12) United States Patent
Gerber et al.

(10) Patent No.: US 9,597,440 B2
(45) Date of Patent: *Mar. 21, 2017

(54) FLUID VOLUME MONITORING FOR PATIENTS WITH RENAL DISEASE

(71) Applicant: Medtronic, Inc., Minneapolis, MN (US)

(72) Inventors: Martin Gerber, Maple Grove, MN (US); John Burnes, Coon Rapids, MN (US); Suping Lyu, Maple Grove, MN (US); VenKatesh R. Manda, Stillwater, MN (US); Bryant Pudil, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 224 days.

This patent is subject to a terminal disclaimer.

(21) Appl. No.: 14/613,725

(22) Filed: Feb. 4, 2015

(65) Prior Publication Data
US 2015/0151033 A1    Jun. 4, 2015

Related U.S. Application Data

(63) Continuation of application No. 13/424,454, filed on Mar. 20, 2012, now Pat. No. 8,951,219.
(Continued)

(51) Int. Cl.
A61M 37/00    (2006.01)
C02F 1/44    (2006.01)
(Continued)

(52) U.S. Cl.
CPC ......... A61M 1/1603 (2014.02); A61B 5/0031 (2013.01); A61B 5/026 (2013.01);
(Continued)

(58) Field of Classification Search
CPC .............. A61M 1/1603; A61M 1/1605; A61M 1/1607; A61M 2205/04; A61M 2205/3303;
(Continued)

(56) References Cited

U.S. PATENT DOCUMENTS 3,608,729 A    9/1971 Haselden
3,669,878 A    6/1972 Marantz
(Continued)

FOREIGN PATENT DOCUMENTS

EP    266795 A2    11/1987
EP    1124599    5/2000
(Continued)

OTHER PUBLICATIONS

PCT/US2012/034327, International Preliminary Report on Patentability, Oct. 29, 2013.
(Continued)

Primary Examiner — Leslie Deak
(74) Attorney, Agent, or Firm — Roger Hahn; Kenneth Collier

(57) ABSTRACT

A method includes initiating a blood fluid removal session of a patient; monitoring an indicator of tissue fluid volume of the patient, or a portion thereof, during the blood fluid removal session; monitoring an indicator of blood fluid volume of the patient during the blood fluid removal session; determining whether a ratio of the indicator of tissue fluid volume to indicator of blood fluid volume is outside of a predetermined range; and altering the rate of fluid removal during the blood fluid removal session if the ratio is determined to be outside of the predetermined range. A blood fluid removal system may be configured to carry out the method.

21 Claims, 13 Drawing Sheets

Related U.S. Application Data

(60) Provisional application No. 61/480,539, filed on Apr. 29, 2011, provisional application No. 61/480,544, filed on Apr. 29, 2011, provisional application No. 61/480,541, filed on Apr. 29, 2011, provisional application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.
| | | |
|---|---|---|
| *A61M 1/16* | (2006.01) | |
| *A61B 5/145* | (2006.01) | |
| *A61B 5/00* | (2006.01) | |
| *A61B 5/026* | (2006.01) | |
| *A61B 5/053* | (2006.01) | |
| *A61M 1/34* | (2006.01) | |
| *B01D 65/02* | (2006.01) | |
| *A61M 1/00* | (2006.01) | |
| *A61B 5/0295* | (2006.01) | |
| *A61M 1/14* | (2006.01) | |
| *B01D 61/00* | (2006.01) | |
| *B01D 61/32* | (2006.01) | |
| *A61M 1/36* | (2006.01) | |
| *A61M 1/28* | (2006.01) | |

(52) U.S. Cl.
CPC ............ *A61B 5/0295* (2013.01); *A61B 5/053* (2013.01); *A61B 5/0537* (2013.01); *A61B 5/145* (2013.01); *A61B 5/14503* (2013.01); *A61B 5/14535* (2013.01); *A61B 5/14539* (2013.01); *A61B 5/14546* (2013.01); *A61B 5/4836* (2013.01); *A61B 5/4848* (2013.01); *A61B 5/4875* (2013.01); *A61B 5/6866* (2013.01); *A61B 5/7282* (2013.01); *A61M 1/00* (2013.01); *A61M 1/14* (2013.01); *A61M 1/16* (2013.01); *A61M 1/1601* (2014.02); *A61M 1/1605* (2014.02); *A61M 1/1607* (2014.02); *A61M 1/1613* (2014.02); *A61M 1/28* (2013.01); *A61M 1/34* (2013.01); *A61M 1/342* (2013.01); *A61M 1/3607* (2014.02); *A61M 1/3609* (2014.02); *A61M 1/3672* (2013.01); *B01D 61/00* (2013.01); *B01D 61/32* (2013.01); *B01D 65/02* (2013.01); *A61B 2560/0223* (2013.01); *A61M 2202/0498* (2013.01); *A61M 2205/04* (2013.01); *A61M 2205/18* (2013.01); *A61M 2205/33* (2013.01); *A61M 2205/3303* (2013.01); *A61M 2205/3334* (2013.01); *A61M 2205/3523* (2013.01); *A61M 2205/50* (2013.01); *A61M 2205/52* (2013.01); *A61M 2205/60* (2013.01); *A61M 2205/70* (2013.01); *A61M 2230/00* (2013.01); *A61M 2230/005* (2013.01); *A61M 2230/20* (2013.01); *A61M 2230/207* (2013.01); *A61M 2230/208* (2013.01); *A61M 2230/65* (2013.01); *B01D 2321/12* (2013.01); *B01D 2321/40* (2013.01)

(58) Field of Classification Search
CPC ...... A61M 2205/3334; A61M 2205/70; A61B 5/14535; A61B 5/4875; A61B 5/7282; B01D 65/002
USPC ... 604/5.01, 5.04, 6.09, 6.11, 4.01; 210/645, 210/646, 746
See application file for complete search history.

(56) References Cited

U.S. PATENT DOCUMENTS

| | | |
|---|---|---|
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,371,385 A | 2/1983 | Johnson |
| 4,381,999 A | 5/1983 | Boucher |
| 4,460,555 A | 7/1984 | Thompson |
| 4,581,141 A | 4/1986 | Ash |
| 4,650,587 A | 3/1987 | Polak |
| 4,826,663 A | 5/1989 | Alberti |
| 4,828,693 A | 5/1989 | Lindsay |
| 5,284,470 A | 2/1994 | Beltz |
| 5,302,288 A | 4/1994 | Meidl |
| 5,318,750 A | 6/1994 | Lascombes |
| 5,468,388 A | 11/1995 | Goddard |
| 5,762,782 A | 6/1998 | Kenley |
| 5,944,684 A | 8/1999 | Roberts |
| 6,048,732 A | 4/2000 | Anslyn |
| 6,254,567 B1 | 7/2001 | Treu |
| 6,627,164 B1 | 9/2003 | Wong |
| 6,818,196 B2 | 11/2004 | Wong |
| 6,878,283 B2 | 4/2005 | Thompson |
| 6,960,179 B2 | 11/2005 | Gura |
| 7,208,092 B2 | 4/2007 | Micheli |
| 7,276,042 B2 | 10/2007 | Polaschegg |
| 7,566,432 B2 | 7/2009 | Wong |
| 7,575,564 B2 | 8/2009 | Childers |
| 7,704,361 B2 | 4/2010 | Garde |
| 7,736,507 B2 | 6/2010 | Wong |
| 7,776,210 B2 | 8/2010 | Rosenbaum |
| 7,794,141 B2 | 9/2010 | Perry |
| 7,850,635 B2 | 12/2010 | Polaschegg |
| 7,922,911 B2 | 4/2011 | Micheli |
| 7,947,179 B2 | 5/2011 | Rosenbaum |
| 7,967,022 B2 | 6/2011 | Grant |
| 7,981,082 B2 | 7/2011 | Wang |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,317,492 B2 | 11/2012 | Demers |
| 8,366,316 B2 | 2/2013 | Kamen |
| 8,366,655 B2 | 2/2013 | Kamen |
| 1,383,728 A1 | 3/2013 | Pudil |
| 8,409,441 B2 | 4/2013 | Wilt |
| 8,499,780 B2 | 8/2013 | Wilt |
| 8,535,525 B2 | 9/2013 | Heyes |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 2002/0112609 A1 | 8/2002 | Wong |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2004/0099593 A1 | 5/2004 | DePaolis |
| 2004/0147900 A1 | 7/2004 | Polaschegg |
| 2005/0113796 A1 | 5/2005 | Taylor |
| 2005/0126998 A1 | 6/2005 | Childers |
| 2005/0150832 A1 | 7/2005 | Tsukamoto |
| 2005/0274658 A1 | 12/2005 | Rosenbaum |
| 2006/0195064 A1 | 8/2006 | Plahey |
| 2007/0007208 A1 | 1/2007 | Brugger |
| 2007/0138011 A1 | 6/2007 | Hofmann |
| 2007/0179431 A1 | 8/2007 | Roberts |
| 2008/0006570 A1 | 1/2008 | Gura |
| 2008/0053905 A9 | 3/2008 | Brugger |
| 2009/0020471 A1 | 1/2009 | Tsukamoto |
| 2009/0127193 A1 | 5/2009 | Updyke |

(56) References Cited

U.S. PATENT DOCUMENTS

| | | |
|---|---|---|
| 2009/0281484 A1 | 11/2009 | Childers |
| 2009/0282980 A1 | 11/2009 | Gura |
| 2010/0004588 A1 | 1/2010 | Yeh |
| 2010/0078381 A1 | 4/2010 | Merchant |
| 2010/0078387 A1 | 4/2010 | Wong |
| 2010/0084330 A1 | 4/2010 | Wong |
| 2010/0114012 A1 | 5/2010 | Sandford |
| 2010/0217181 A1 | 8/2010 | Roberts |
| 2011/0017665 A1 | 1/2011 | Updyke |
| 2011/0087187 A1 | 4/2011 | Beck |
| 2011/0184340 A1 | 7/2011 | Tan |
| 2011/0272337 A1 | 11/2011 | Palmer |
| 2012/0083729 A1 | 4/2012 | Childers |
| 2012/0115248 A1 | 5/2012 | Ansyln |
| 2013/0037465 A1 | 2/2013 | Heyes |
| 2013/0199998 A1 | 8/2013 | Kelly |
| 2013/0274642 A1 | 10/2013 | Soykan |
| 2013/0324915 A1 | 12/2013 | Britton |
| 2013/0330208 A1 | 12/2013 | Ly |
| 2013/0331774 A1 | 12/2013 | Farrell |
| 2014/0018728 A1 | 1/2014 | Plahey |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |

FOREIGN PATENT DOCUMENTS

| | | |
|---|---|---|
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| JP | 5099464 | 10/2012 |
| WO | 9937342 | 7/1999 |
| WO | 0057935 | 10/2000 |
| WO | 0066197 | 11/2000 |
| WO | 0066197 A1 | 11/2000 |
| WO | 0170307 A1 | 9/2001 |
| WO | 0185295 A2 | 9/2001 |
| WO | 0185295 | 11/2001 |
| WO | 03043677 A2 | 5/2003 |
| WO | 03043680 | 5/2003 |
| WO | 03051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2005061026 | 7/2005 |
| WO | 2005123230 A2 | 12/2005 |
| WO | 2007089855 A2 | 8/2007 |
| WO | 2008037410 | 4/2008 |
| WO | 2009024566 | 2/2009 |
| WO | 2009026603 | 3/2009 |
| WO | 2009026603 A1 | 3/2009 |
| WO | 2009061608 | 5/2009 |
| WO | 2009094184 | 7/2009 |
| WO | 2009157877 | 12/2009 |
| WO | 2009157878 | 12/2009 |
| WO | 2010028860 | 3/2010 |
| WO | 2010096659 | 10/2010 |
| WO | 2010121820 | 10/2010 |
| WO | 2011025705 | 3/2011 |
| WO | 2011025705 A1 | 3/2011 |
| WO | 2011137693 | 11/2011 |
| WO | 2012042323 | 4/2012 |
| WO | 2012050781 | 4/2012 |
| WO | 2012051996 | 4/2012 |
| WO | 2012073420 | 7/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A | 8/2013 |
| WO | 2013121162 A1 | 8/2013 |
| WO | 2013140346 | 9/2013 |
| WO | 2013141896 | 9/2013 |
| WO | 2013101292 A3 | 10/2013 |
| WO | 2014066254 | 5/2014 |
| WO | 2014066255 | 5/2014 |
| WO | 2014077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

PCT/US2012/034329, Intenational Preliminary Report on Patentability, Oct. 29, 2013.

PCT/US2012/034330, International Preliminary Report on Patentability, Oct. 29, 2013.

Redfield, et. al, Restoration of renal response to atria! natriuretic factor in experimental low-output heat failure, Am. J. Physiol., 1989, R917-923:257.

Rogoza, et. al., Validation of A&D UA-767 device for the self-measurement of blood pressure, Blood Pressure Monitoring, 2000, 227-231, 5(4).

Ronco, et. al., Cardiorenal Syndrome, J. Am. Coll. Cardiol., 2008, 1527-1539:52.

PCT/US2012/034329, International Preliminary Report on Patentability, Oct. 29, 2013.

Lima, et. al., An electrochemical sensor based on nanostructure hollsndite-type manganese oxide for detection of potassium ion, Sensors, 2009, 6613-8625, 9.

MacLean, et, al., Effects of hindlimb contraction on pressor and muscle interstitial metabolite responses in the cat, J. App. Physiol., 1998, 1583-1592, 85 (4).

Coast, et al. 1990, An approach to Cardiac Arrhythmia analysis Using Hidden Markov Models, IEEE Transactions on Biomedical Engineering. 1990, 37 (9):826-835.

PCT Application, PCT/US20013/020404, filed Jan. 4, 2013.

U.S. Appl. No. 14/261,651, filed Apr. 25, 2014.

U.S. Appl. No. 14/259,655, filed Apr. 23, 2014.

U.S. Appl. No. 14/259,589, filed Apr. 23, 2014.

(56) References Cited

OTHER PUBLICATIONS

Leifer, I., et al., A Study on the Temperature Variation of Rise Velocity for Large Clean Bubbles, J. Atmospheric & Oceanic Tech., vol. 17, pp. 1392-1402.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Nedelkov, et. al., Design of buffer exchange surfaces and sensor chips for biosensor chip mass spectrometry, Proteomics, 2002, 441-446, 2(4).
PCT/US/2012/034327, International Search Report, Aug. 13, 2013.
PCT/US/2012/034329, International Search Report, Dec. 3, 2012.
PCT/US2012/034331, International Search Report, Jul. 9, 2012.
PCT/US2012/034334, International Search Report, Jul. 6, 2012.
PCT/US2012/034335, International Search Report, Sep. 5, 2012.
Roberts M, The regenerative dialysis (REDY) sorbent system. Nephrology, 1998, 275-278:4.
Siegenthalar, et. al., Pulmonary fluid status monitoring with intrathoracic impedance, Journal of Cli.
Zhong, et. al., Miniature urea sensor based on H(+)-ion sensitive field effect transistor and its application in clinical analysis, Chin. J. Biotechnol., 1992, 57-65. 8(1).
Overgaard, et. al., Activity-induced recovery of excitability in K+-depressed rat soieus muscle, Am. J. P.
Overgaard. et. al., Relations between excitability and contractility in rate soleus'muscle: role of the NA+-K+pump and NA+-K-S gradients. Journal of Physiology, 1999, 215-225, 518(1).
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
The FHN Trial Group. In-Center. Hemodialysis Six Times per Week versus Three Times per Week, New England Journal of Medicine, 2010.
PCT/US2014/014357 International Search Report and Written Opinion.
Roberts M, The regenerative dialysis (REDY) sorbent system, Nephrology, 1998, 275-278 : 4.
Bleyer, et. al., Sudden and cardiac death rates in hemodialysis patients, Kidney International, 1999, 1553-1559 : 55.
Wang, Fundamentals of intrathoracic impedance monitoring in heart failure, Am. J. Cardiology, 2007, 3G-310: Suppl.
PCT/US2012/034330, International Search Report, Aug. 28, 2012.
PCT/US2012/034332, International Search Report, Jul. 5, 2012.
Ronco, et. al., "Cardiorenal Syndrome", J. Am. Coll. Cardiol., 2008, 1527-1539 : 52.
Secemsky, et. al, High prevalence of cardiac autonomic dysfunction and T-wave alternans in dialysis patients. Heart Rhythm, Apr. 2011, 592-598 : vol. 8, No. 4.
Wang, Fundamentals of intrathoracic impedance monitoring in heart failure, Am. J. Cardiology, 2007, 3G-10G : Suppl.
Wei, et. al., Fullerene-cryptand coated piezoelectric crystal urea sensor based on urease, Analytica Chimica Acta, 2001,77-85:437.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
PCT/US2012/034335, International Preliminary Report on Patentability, Nov. 7, 2013.
PCT/US2012/034303, Internationa Search Report, Jul. 6, 2013.
PCT/US2012/034332, Internatonal Preliminary Report on Patentability, Oct. 29, 2013.
PCT/US2012/034333, International Preliminary Report on Patentability, Oct. 29, 2013.
PCT/US2012/034333, International Search Report, Aug. 29, 2013.
Talaia, MAR, Terminal Velocity of a Bubble Rise in a Liquid Column, Talaia, World Acad. of Sci., Engineering & Tech., vol. 28, pp. 264-268.

FLUID VOLUME MONITORING FOR PATIENTS WITH RENAL DISEASE

RELATED APPLICATION

This application claims priority to U.S. application Ser. No. 13/424,454, filed on Mar. 20, 2012, U.S. Provisional Application No. 61/480,539, U.S. Provisional Application No. 61/480,544, U.S. Provisional Application No. 61/480,541, U.S. Provisional Application No. 61/480,535, U.S. Provisional Application No. 61/480,532, U.S. Provisional Application No. 61/480,530, and U.S. Provisional Application No. 61/480,528, wherein each provisional priority application was filed Apr. 29, 2011, wherein each priority application is hereby incorporated by reference in its entirety to the extent that it does not conflict with the disclosure presented herein.

FIELD

The present disclosure relates generally to devices, systems and methods for monitoring fluid volume in patients with renal diseases, such as patients undergoing hemodialysis and ultrafiltration, and in monitoring balance between blood fluid volume and tissue fluid volume.

BACKGROUND

Hemodialysis and ultrafiltration share removal of excess fluid as a primary goal. The amount of fluid to be removed is determined before a treatment session and is related to the patient's pre-treatment weight, fluid addition during treatment and their theoretical dry weight. The amount of fluid to remove and the rate of removal is set on the dialysis or filtration machine and confirmed gravimetrically.

However, it can be difficult to accurately determine a patient's dry weight, which is considered to be the weight that the person would be if their kidneys were properly functioning. What a given patient might weigh if their kidneys were properly functioning is often an unknown variable and can change over time. Yet an accurate determination of the patient's dry weight is important to the successful outcome of a fluid removal session.

Unfortunately, the patient's dry weight is not typically calculated or re-evaluated frequently. Unlike the patient's actual weight, which is measured before and after a fluid removal session, dry weight is often determined much less frequently; e.g. monthly, and much can change in the time between a dry weight determination and a given fluid removal session, which typically occurs three times a week. While being an important variable in fluid removal considerations, dry weight is often difficult to calculate and may vary between sessions.

Errors in fluid volume removal can result in severe hypotension and patient crashing following or during hemodialysis treatment. Sudden and cardiac death (including death from congestive heart failure, myocardial infarction, and sudden death) are common in hemodialysis patients. See Bleyer et al, "Sudden and cardiac death rated in hemodialysis patients," *Kidney International*, (1999), 55:1552-1559.

In part to avoid such sudden death, fluid removal rate can be adjusted during a hemodialysis session to prevent too rapid removal or to achieve a specific removal profile. The removal rate is controlled by adjusting pump parameters, and the amount of fluid removed is confirmed gravimetrically (i.e., by weighing). However, current standard-of-care hemodialysis does not include any monitoring of fluid volume within the tissue to get an accurate reading of actual fluid status. Some suggestions have been made to monitor hematocrit levels during dialysis to monitor blood volume in an attempt to avoid the potentially dire consequences of fluid imbalance. However, monitoring blood fluid volume alone may not present as accurate of a picture as monitoring the ratio of blood to tissue volume and ensuring the ratio stays within predefined parameters during hemodialysis for purposes of patient safety.

SUMMARY

This disclosure, among other things, describes devices, systems and methods for monitoring fluid volume in blood and tissue compartments of patients during fluid removal sessions, such as hemodialysis, ultrafiltration, or the like, and controlling the rate at which fluid is removed from blood based on the monitored fluid volumes. By monitoring tissue fluid volume and blood fluid volume, the rate of fluid removal from blood during a blood cleaning session may be adjusted to maintain an acceptable balance of fluid between blood and tissue to enhance patient safety and increase efficiency of blood cleaning.

In various embodiments described herein, a method includes (i) initiating a blood fluid removal session of a patient; (ii) monitoring an indicator of tissue fluid volume of the patient, or a portion thereof, during the blood fluid removal session; (iii) monitoring an indicator of blood fluid volume of the patient during the blood fluid removal session; (iv) determining whether a ratio of the indicator of tissue fluid volume to indicator of blood fluid volume is outside of a predetermined range; and (v) altering the rate of fluid removal during the blood fluid removal session if the ratio is determined to be outside of the predetermined range.

In numerous embodiments described herein, a system includes a blood fluid removal device having (i) an inlet for receiving blood from a patient, (ii) a first outlet for returning reduced fluid blood to the patient, (iii) a medium for removing fluid from the blood, the medium being positioned between the inlet and the first outlet, (iv) a fluid rate removal controller; and (v) a second outlet for flow of the removed fluid and contaminants. The system also includes (i) a first sensor for monitoring an indicator of tissue fluid volume; (ii) a second sensor for monitoring an indicator of blood fluid volume; and (iii) a processor in operable communication with the sensor for monitoring an indicator of tissue fluid volume, the sensor for monitoring an indicator of blood fluid volume; and the fluid rate removal controller. The processor is configured to adjust the rate at which fluid is removed based on data obtained from the first sensor and the second sensor.

One or more embodiments of the systems, devices and methods described herein may provide one or more advantages over prior systems, devices and methods for blood fluid removal in patients. Such advantages will be apparent to those of skilled in the art upon reading the following detailed description.

In any embodiment, the invention can be drawn to a method. In any embodiment, the method can comprise the steps of initiating a blood fluid removal session of a patient with an initial blood fluid removal rate; monitoring an indicator of tissue fluid volume of the patient during the blood fluid removal session; monitoring an indicator of blood fluid volume of the patient during the blood fluid removal session; determining a first indicator of tissue fluid volume and a first indicator of blood fluid volume; acquiring a first set of data regarding the physiological health of the patient; altering the rate of blood fluid removal to a second blood fluid removal rate; determining a second indicator of tissue fluid volume and a second indicator of blood fluid volume; acquiring a second set of data regarding the physiological health of the patient; determining a preferable outcome measure based on the first and second sets of physiological data; and altering the rate of blood fluid removal so that an indicator of tissue fluid volume and an indicator of blood fluid volume are within a pre-determined range of the preferable outcome measure.

In any embodiment, the outcome measure can be any one of a degree of hypotension, a deviation from dry weight, or combinations thereof.

In any embodiment, the method can comprise determining a ratio of the indicator of blood fluid volume to the indicator of tissue fluid volume; and altering the rate of blood fluid removal so that the ratio of the indicator of tissue fluid volume to the indicator of blood fluid volume is within a pre-determined range of the preferable outcome measure.

In any embodiment, the method can comprise determining whether the indicator of tissue fluid volume or the indicator of blood fluid volume crosses a predetermined threshold during the blood fluid removal session.

In any embodiment, if the indicator of blood fluid volume or the indicator of tissue fluid volume crosses the predetermined threshold, the method can comprise altering the rate of blood fluid removal.

In any embodiment, the indicator of tissue fluid volume can be tissue impedance.

In any embodiment, the indicator of blood fluid volume can be a hematocrit level, or an indicator thereof.

In any embodiment, measuring the hematocrit level can comprise measuring oxygenated hemoglobin concentration.

In any embodiment, one or both of the indicator of tissue fluid volume and the indicator of blood fluid volume can be measured with one or more implantable sensors.

In any embodiment, the blood fluid removal session can be carried out with an implantable blood fluid removal device.

In any embodiment, the blood fluid removal session can be carried out with a wearable blood fluid removal device.

In any embodiment, if the indicator of tissue fluid volume or the indicator of blood fluid volume is outside of a pre-determined range, an alert can be provided.

In any embodiment, a method carried out by a blood fluid removal system can comprise initiating a blood fluid removal session of a patient; monitoring an indicator of tissue fluid volume of the patient, or a portion thereof, during the blood fluid removal session; monitoring an indicator of blood fluid volume of the patient during the blood fluid removal session; determining whether the indicator of tissue fluid volume and the indicator of blood fluid volume are outside of a predetermined range; and altering the rate that replacement fluid is added to the blood if the indicator of tissue fluid volume or the indicator of blood volume is determined to be outside of the predetermined range.

In any embodiment, the replacement fluid can be added to the blood prior to fluid being removed from the blood.

In any embodiment, the replacement fluid can be added to the blood after fluid being removed from the blood.

In any embodiment, the method can comprise obtaining a ratio of the indicator of tissue fluid volume to the indicator of blood fluid volume; determining whether the ratio of the indicator of tissue fluid volume to the indicator of blood fluid volume is outside of a predetermined range; and altering the rate that the replacement fluid is added to the blood if the ratio of the indicator of tissue fluid volume to the indicator of blood fluid volume is outside of the predetermined range.

In any embodiment, if the indicator of tissue fluid volume or the indicator of blood fluid volume is outside of a pre-determined range, an alert can be provided.

In any embodiment, the method can comprise altering a rate of blood fluid removal if the indicator of tissue fluid volume or the indicator of blood volume is determined to be outside of the predetermined range.

The invention is also drawn to a system. In any embodiment, the system can comprise a blood fluid removal device comprising i) an inlet for receiving blood from a patient, (ii) a first outlet for returning blood from the patient; (iii) a medium for removing fluid and contaminants from the blood, the medium being positioned between the inlet and the first outlet, (iv) a fluid rate removal controller; and (v) a second outlet for flow of the removed fluid and contaminants; a first sensor for monitoring an indicator of tissue fluid volume; a second sensor for monitoring an indicator of blood fluid volume; and control electronics in operable communication with the sensor for monitoring an indicator of tissue fluid volume, the sensor for monitoring an indicator of blood fluid volume; and the fluid rate removal controller; wherein the control electronics are configured to carry out the methods described herein.

In any embodiment of the system, the medium for removal of fluid and contaminants from the blood can comprise a filtration membrane.

In any embodiment of the system, one or more components of the first sensor, the second sensor and the control electronics can be housed within the blood fluid removal device.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
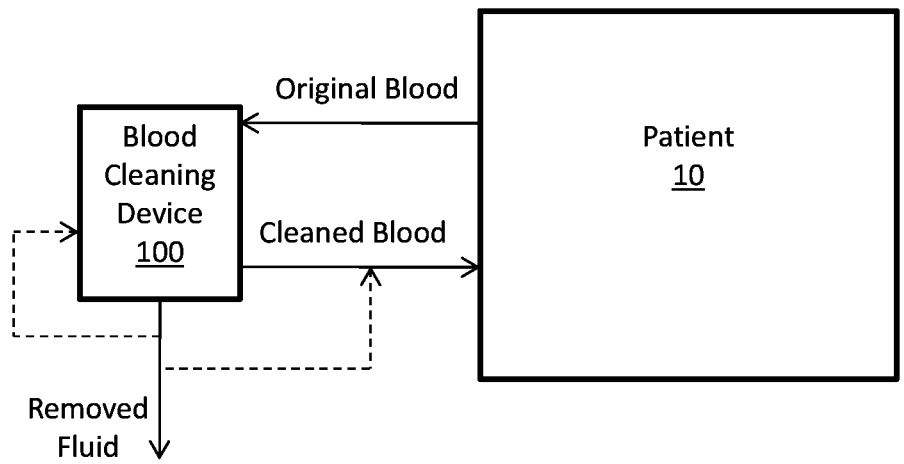
FIGS. 1-4 are schematic block diagrams showing interaction of blood fluid removal devices with a patient showing flow of blood (dashed arrows) and fluid (solid arrows), which blood fluid removal devices may be used in various embodiments described herein.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, "tissue fluid volume" means the volume of fluid (as opposed to cells or solids) in a tissue or region of a patient, which can be the entire patient. Tissue "fluid" is often referred to as interstitial fluid. In various embodiments, one or more of tissue fluid volume, rate of change of tissue fluid volume, or the like are monitored in accordance with the teaching presented herein.

As used herein, "blood fluid volume" means the volume or percentage of blood volume that is occupied by fluid, as opposed to cells or solids in the blood. In various embodiments, one or more of blood fluid volume, rate of change of blood fluid volume, or the like are monitored in accordance with the teaching presented herein.

As used herein, a "blood fluid removal process," or the like, refers to a process from which fluid is removed from blood of a patient and the blood is returned to the patient. In most cases, the blood is also cleaned; i.e., waste products are removed from the blood and cleaned blood is returned to the patient. Examples of blood fluid removal processes include ultrafiltration, hemofiltration, hemodialysis, hemodiafiltration, peritoneal dialysis and the like. Any patient for which blood fluid removal is indicated may benefit from the devices, systems and methods described herein.

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute kidney failure. Often such patients are stage 3 to stage 5 chronic kidney disease patients, are unresponsive or under-responsive to diuretics, or the like.

This disclosure relates to, among other things, systems and methods for maintaining a proper fluid balance between the blood compartment and the tissue compartment during a blood fluid removal session. Sensors are used to monitor tissue fluid volume and blood fluid volume, and based on acquired data, the rate of fluid removal during a blood fluid removal procedure is adjusted to ensure a proper fluid balance between the two compartments and to optimize of treatment time.

Any suitable device or system for removing fluid, or fluid and contaminants, from blood may be used in accordance with the teachings presented herein. The devices, or components thereof, may be traditional large counsel-type, wearable, or implantable.

Block diagrams of some examples devices and systems are shown in FIGS. 1-4. As shown in FIG. 1, blood may be removed from a patient 10 and fluid may be removed via a blood fluid removal device 100 and returned to the patient 10. Removed fluid may be diverted. In some embodiments where the blood fluid removal device 100 or system, or components thereof, are implanted, the removed fluid may be diverted to the patient's bladder. Examples of blood fluid removal devices 100 that may operate as depicted in FIG. 1 are ultrafiltration and hemofiltration devices. Examples of such devices and components thereof that may be employed in accordance with the teachings presented herein are well known in the art. It will be understood that peritoneal dialysis, where dialysate is introduced into the peritoneal cavity, may also be employed. The dashed lines in FIG. 1 indicate that, in some embodiments, (i) removed fluid may be reintroduced or collected and reintroduced into blood of a patient to avoid, mitigate or correct a hypotensive event, or (ii) may be back filtered through the blood cleaning device 100.

Figure 2:
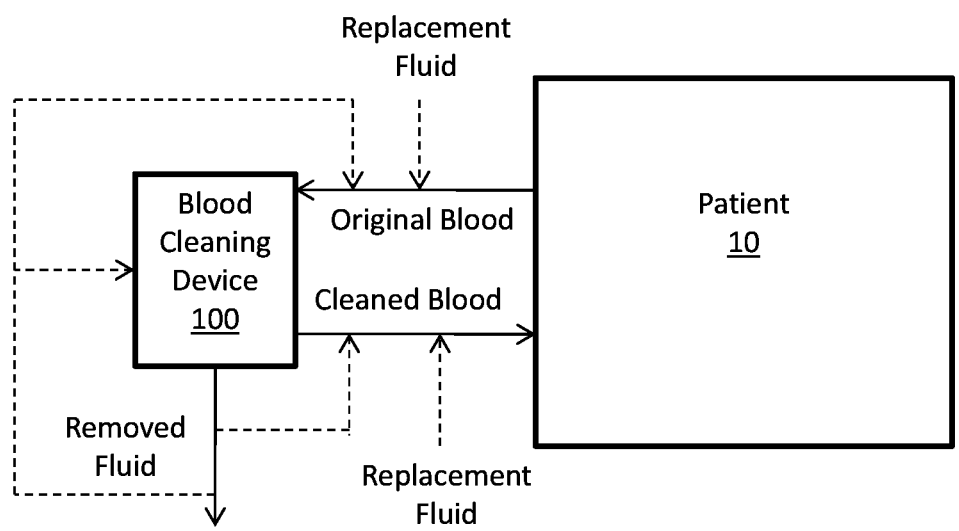

With some of such devices, fluid may be removed at too great of a rate. Accordingly and with reference to FIG. 2, replacement fluid may be introduced into the patient's blood. As shown in FIG. 2, the replacement fluid may be added to the original blood before fluid removal or may be added to the blood after initial fluid removal and prior to return to the patient's cardiovascular system. Preferably, the replacement fluid is added after initial fluid removal. Replacement fluid or removed fluid may be introduced into blood of a patient to avoid, mitigate or correct a hypotensive event; e.g. as may be detected by systems described herein. Of course, as discussed above with regard to FIG. 1 and as shown in FIG. 2, removed fluid may be back-filtered through the blood cleaning device 100.

Figure 3:
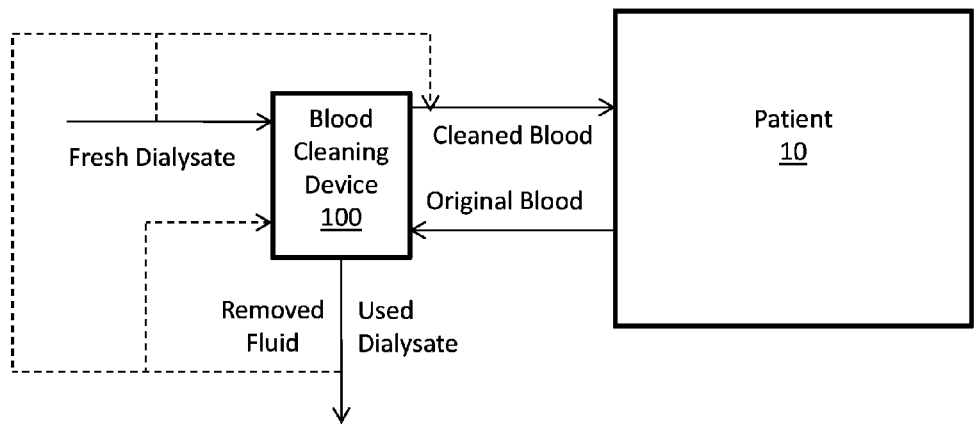

As shown in the embodiment depicted in FIG. 3, the blood fluid removal device 100 may employ dialysate to assist in removal of contaminants from the patient's blood and in maintaining proper pH and electrolyte balance. Used dialysate and fluid removed from the blood may be diverted. In some embodiments, particularly where the blood fluid removal device 100 or system or components thereof are wearable or implantable, the used dialysate and removed fluid, or a portion thereof, may be regenerated to produce fresh dialysate for re-use in the blood fluid removal process.

One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. Systems and devices that operate in a manner shown in the embodiment of FIG. 3 include hemodialysis and hemodiafiltration systems. Examples of such devices and components thereof that may be employed in accordance with the teachings presented herein are well known in the art. Fresh dialysate, used dialysate or removed fluid may be introduced into blood as may be needed or desired; e.g., to avoid, mitigate or correct a hypotensive event. Again, removed fluid may be back filtered through blood cleaning device 100.

Figure 4:
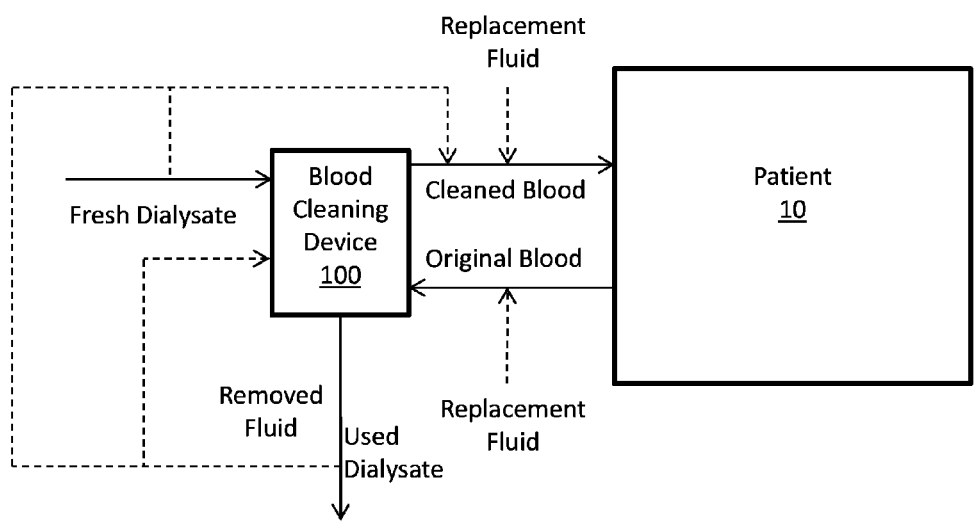

As shown in FIG. 4, in cases where the blood fluid removal device 100 of FIG. 3 removes fluid from the blood at too high of a rate, replacement fluid may be introduced into the patient's blood, upstream or downstream of fluid removal.

Regardless of the device or blood fluid removal process employed, it is important to control the amount and rate of fluid removal to avoid severe hypotension, heart failure or sudden cardiac death in patients from whom blood fluid is removed. It is also important to control the amount and rate of fluid removal for purposes of efficiency. That is, even though it may be generally safer to remove fluid very slowly, such slow removal may result in blood fluid removal sessions that last for considerable periods of time. While such slow removal may be acceptable for blood fluid removal systems that are wearable or implantable, it may not be acceptable for larger stand alone systems that require a patient visit to a clinic. The patient's quality of life, which is typically already low, may suffer from extended stays in the clinic that would be necessary for systems that slowly remove fluid from the blood. Ideally a blood fluid removal device or system balances the health concerns with the efficiency concerns in controlling the rate of fluid removal.

Of course, the amount of fluid removed is also an important variable in maintenance of patient health. If too little fluid is removed, the patient is burdened with excess fluid, which can lead to heart failure, hypertension, or other disorders, until their next blood fluid removal session or until their fluid removal prescription is changed. If too much fluid is removed, the patient may suffer from hypotension, crashing, sudden cardiac death, or the like. Accordingly, it would be desirable to remove fluid from the blood not only at an acceptable rate, but also in an acceptable amount.

Figure 5:
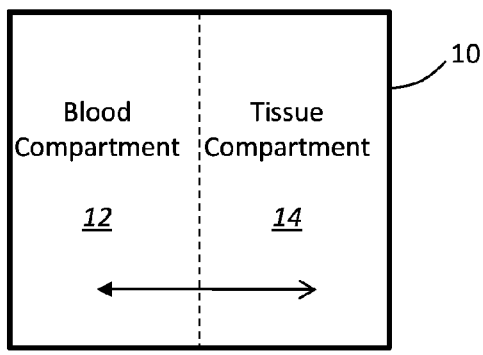
FIGS. 5-7 are schematic block diagrams of fluid flow between the blood compartment and the tissue compartment of a patient that are presented to facilitate understanding of certain principles described herein.
Figure 6:
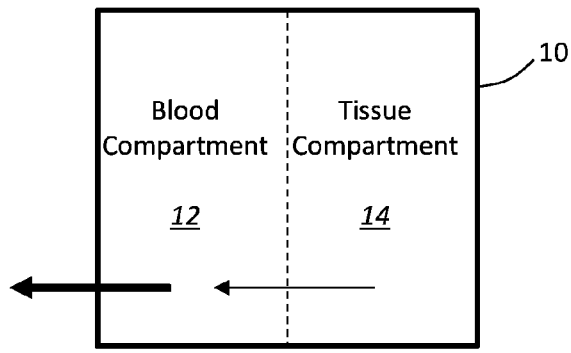
Figure 7:
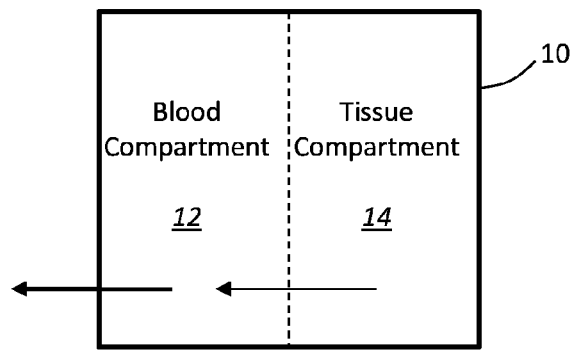

Referring now to FIGS. 5-7 relationships between fluid volume in the tissue compartment 14 and the blood compartment 12 in a patient 10 are shown. As shown in FIG. 5, absent fluid removal from either compartment, equilibrium of fluid flow and volume (indicated by arrow) is reached between the tissue compartment 14 and the blood compartment 12. As shown in FIGS. 6-7, removal of fluid from the blood compartment 12 through a blood fluid removal process, such as hemodialysis or ultrafiltration, causes a shift in flow of fluid from the tissue compartment 14 into the blood compartment 12. However, if the rate of fluid removal from the blood compartment 12 is too large (see thickness of arrow in FIG. 6), the rate of fluid flow from the tissue compartment (see thickness of arrow in FIG. 6) may not be sufficient to keep up with the rate of fluid loss from the blood compartment 12, putting the patient's well-being in jeopardy. A more moderate differential of fluid loss between compartments (see, e.g., FIG. 7) may be desired from a patient health perspective. Of course, as described above, it may be desirable to maximize the fluid removal rate from blood, as long as it is safe, to increase the efficiency of the blood fluid removal process and reduce the time the patient is subjected to the fluid removal procedure.

In embodiments, agents that increase the osmolality of dialysate (if used) and thus blood, may be used to increase the rate at which fluid is transferred from the tissue compartment to the blood compartment of the patient. That is, by increasing the concentration of osmolality enhancer in the dialysate, fluid may be removed from blood at a higher rate. However, if the osmolality enhancer can also pass through the dialysis membrane and increase in concentration in the blood, the blood returned to the patient may have a higher osmolality than the blood removed from the patient. And, blood having a higher osmolality will tend to result in more rapid fluid removal from the tissue into the blood. The concentration of the osmolality enhancer used in the dialysate may be changed over the course of a session; e.g., higher concentration at the beginning and lower concentration at the end. Examples of osmolality enhancers that may be employed include sodium and glucose. Of course, other osmolality enhancers may be used.

To enhance patient safety or efficiency, it may be desirable to monitor fluid loss from, or volume in, both the tissue compartment 14 and the blood compartment 12 and to determine whether the relative losses or volumes are within a safe range. Suitable ratios of tissue fluid volume to blood fluid volume may be determined on a patient-by-patient basis or may be set initially according to population statistics. As a general rule, decreases in blood volume at a rate of 8 to 10% per hour can cause imminent hypovolaemia. Accordingly, for most patients the rate of fluid removal from blood should be set at less than 8 to 10% per hour. Of course, higher rates may be employed if an osmolality enhancer, such as sodium, is used to enhance the rate of fluid transfer from tissue into blood.

Appropriate tissue fluid volumes can initially be accounted for based on normal blood and normal total volume, or dry weight. Dry weight can be based on patient height, weight, gender, body composition, or blood pressure. Dry weight may also be determined during a fluid removal sessions by monitoring blood pressure and when discomfort, such as cramping, occurs. A value of monitored indicator of tissue fluid volume may be set so as not to exceed a monitored value of fluid removal at the determined dry weight. Based on these initial settings and monitored indicators, an appropriate fluid volume ratio may be based on the rate and direction of fluid transfer from tissue to the blood. In any case, once appropriate rates of fluid removal are determined, monitored tissue fluid volumes (or indicators thereof) may be used in conjunction with monitored blood fluid volumes (or indicators thereof) to ensure that proper ratios are maintained.

Figure 8:
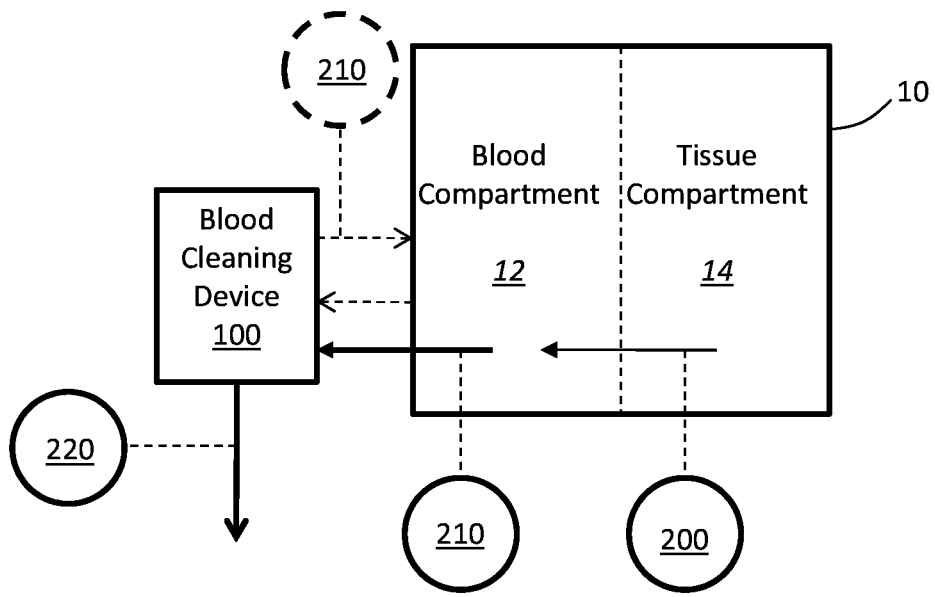
FIG. 8 is a schematic block diagram showing flow of blood (dashed arrows) and fluid (solid arrows) between the tissue compartment and the blood compartment of a patient and a blood fluid removal device, as well as showing potential location of monitoring of fluid in accordance with various embodiments presented herein.

Referring now to FIG. 8, fluid flow loss or fluid volume of the tissue compartment 14, the blood compartment 12, or the fluid loss through the blood fluid removal device 100 may be monitored to ensure that appropriate ratios of fluid are maintained in the blood compartment 12 and the tissue compartment 14 during a blood fluid removal session. One or more sensors 200, 210, 220 or the like may be employed to monitor the fluid flow or volume at one or more of these locations. For example, sensor 200 may be used to monitor tissue fluid volume, sensor 210 may be used to monitor blood fluid volume, and sensor 220 may be used to monitor fluid flow or volume diverted from blood.

In situations where replacement fluid is introduced into blood to compensate for fluid removed from blood (see, e.g., FIGS. 2 and 4 and relevant discussion above), it may be desirable to monitor blood fluid volume at a point after such fluid is added. As depicted by the dashed sensor 210, the blood fluid volume of blood to be returned to the patient 10 may be monitored. Of course, it may be desirable to monitor blood fluid volume as it leaves the patient 10 and as it is returned to the patient. The difference in blood fluid volume will determine the effective fluid loss from the blood compartment 12. That is, the fluid removed from the blood during the blood fluid removal process may be greater than the overall fluid loss of the blood compartment 12 as some fluid may be added to the blood prior to return to the patient.

In some embodiments, sensor 220 may be used to determine fluid loss from the blood compartment 12. In situations where the fluid extracted from the blood is diverted with used dialysate (see, e.g., FIGS. 3-4 and relevant discussion above), the difference in fluid volume between (i) used dialysate and blood fluid removed and (ii) fresh dialysate introduced may be used to determine the volume of fluid extracted. Also, the addition of fluid to the blood before it is returned to the patient (see, e.g., FIGS. 2 and 4 and relevant discussion above) can be accounted for in determining how much fluid is removed from the blood compartment 12.

Any suitable sensor may be used to monitor fluid loss, rate of fluid loss, or fluid volume. Typically, the sensors measure fluid volume indirectly, and thus directly monitor an indicator of fluid volume. For example, in some embodiments, sensor 210 indirectly monitors hematocrit (the portion of blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used. A typical hematocrit level for a healthy adult male is between about 40% and 54%, or about 48%, and a typical level for a healthy adult female is between about 37% and 47%, or about 42%. Prior to a blood fluid removal session, the fluid volume of blood of a kidney disease patient may be elevated, thus hematocrit levels may be lower than desired. It may be desirable for hemotocrit levels to be within 10% or 5% of hematocrit levels of healthy individuals at the end of a blood fluid removal session. Accordingly, blood fluid volumes will be within about 10% or 5% of those of a typical healthy individual.

Hematocrit levels, or an approximation or indicator of hematocrit levels, can thus be used to monitor blood fluid volume. In some embodiments, hemoglobin levels are monitored as an indicator of hematocrit levels and blood fluid volume, as hemoglobin concentration is typically proportional to red blood cell concentration. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In some embodiments, the sensor 210 is implanted in a patient and disposed about a blood vessel to measure hemoglobin levels, and thus hematocrit and blood fluid levels.

Figure 9:
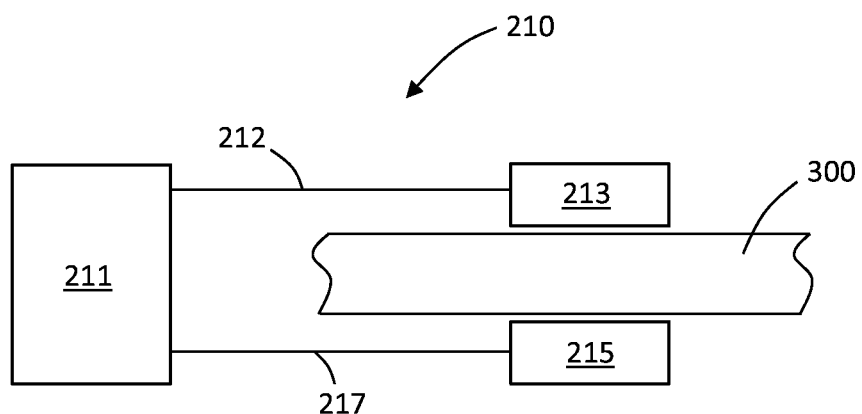
FIG. 9 is a schematic block diagram of selected components of a sensor for monitoring an indicator of blood fluid volume in relation to tubing.

By way of example and with reference to FIG. 9, a schematic diagram of a sensor 210 and tubing 300, which may be a blood vessel, are shown. A light source 213 of appropriate wavelength (red or infrared) is positioned on one side of tubing 300 such that the light passing through tubing 300 hits detector 215. More light is absorbed (and less hits the detector 215) if a higher concentration of hemoglobin is present in tubing 300. A lead 212 carries power and other electrical signals, if appropriate, to the light source 213 from the sensor device body 211, which may contain the power source and other control or detecting electronics. Lead 217 carries electrical signals from detector 215 to the components housed in sensor device body 211.

Regardless of the placement of the sensor 210, the sensor may be calibrated by monitoring flow of blood having known hematocrit levels through tubing 300 (whether a blood vessel or tubing for use with a blood fluid removal device). The values obtained may be stored in a lookup table for reference during a blood fluid removal session or as otherwise needed while the sensor is in use. In some embodiments, the rate of change of blood fluid volume may be determined by comparing the rate of change in light absorbance; e.g., as the fluid is removed from the blood.

The discussion above with regard to hemoglobin sensing is provided as an example of how known sensing technologies and components may be employed in accordance with the teachings presented herein with regard to blood fluid volume monitoring. It will be understood that other technologies and components may be used to monitor blood fluid volume. For example, total blood protein or albumin concentrations and blood pressure, alone or in combination, can be used to evaluate blood volume. By way of example, high blood pressure combined with low hematocrit or low blood protein indicates a higher possibility of blood fluid overloading. Alternatively or additionally, blood viscosity may be used as an indicator of blood fluid volume and may be measured by pressure or flow.

Figure 10:
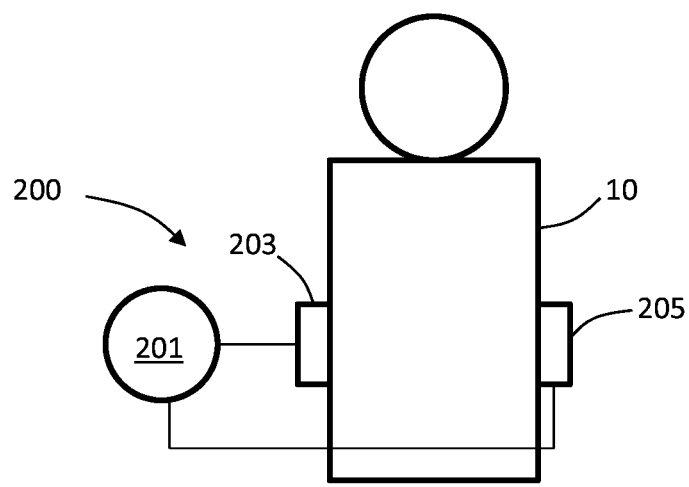
FIGS. 10-11 are schematic block diagrams of selected components of impedance sensors, external to (FIG. 10) and implanted in (FIG. 11) a patient.
Figure 11:
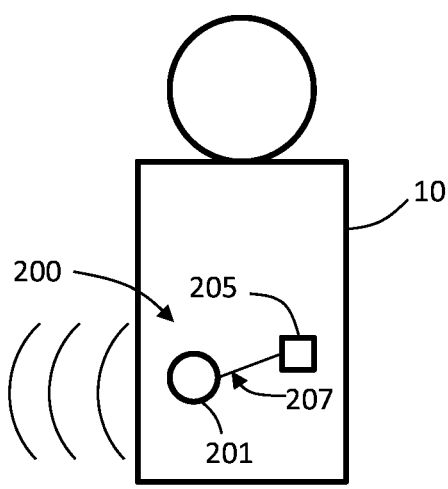

Referring again to FIG. 8 and with regard to monitoring fluid volume in a tissue compartment 14 of a patient 10, any suitable sensor 200 may be employed. By way of example, impedance of flow of current through a tissue of a patient may be monitored as an indicator of fluid volume in the tissue. With reference to FIGS. 10-11, the impedance sensor 200 may be external (FIG. 10) or implantable (FIG. 11). As fluid volume rises in the tissue, impedance is decreased. It will be understood that capacitance, dielectric constant, and other similar measures may also be used, as these are correlated to impedance. For the purposes of this disclosure, monitoring of electrical properties of a tissue that are correlated to impedance are considered to be subsumed under the definition of monitoring "impedance."

As depicted in FIG. 10, impedance may be monitored between two electrodes 203, 205. The electrodes 203, 205 are operably coupled to control and processing electronics 201 via leads. The electronics 201 are configured to generate a voltage differential between the electrodes 203, 205, current may be measured and impedance calculated. The measurement may be done in either DC or AC mode. Impedance or phase angle may be correlated to tissue fluid volume. Suitable external impedance monitors 200 and components that may be used in accordance with the teachings described herein are known and described in the art.

In the example depicted in FIG. 11, a conductive housing containing control electronics 201 serves as a reference electrode to electrode 205. Impedance is monitored in the tissue between the housing and the electrode 205. The electrode 205 is coupled to the control electronics 210 via lead 207. As depicted in FIG. 11, the control electronics 201 are configured to wirelessly communicate with a device external to the patient for purposes of transmitting data regarding monitored impedance. Such wireless communication may also be employed with any other type of implantable sensor.

Tissue impedance sensing for purposes of monitoring tissue fluid volume has been well documented. One example of a well studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values.

In some embodiments, more than one implanted impedance sensor, such as more than one OptiVol® fluid status monitoring system, may be employed. The sensors may be configured or placed to monitor impedance of different tissues, different areas of the same tissue, or the like. Duplication of sensors may provide redundancy in case of sensor failure or as a check on the readings obtained from another sensor. In some cases, tissue fluid changes detected by a sensor may be due to conditions other than chronic heart failure or renal disease. For example, increased lung fluid may result from pneumonia. Such fluid may not be indicative of a need for a blood fluid removal session. By having a second impedance sensor placed to monitor, e.g., abdominal fluid, a check may be placed on the sensor placed and configured to monitor lung fluid volume. The sensors may be configured to communicate with each other or another device to determine whether the sensor readings are significantly different.

The discussion above with regard to impedance monitoring is provided as an example of how known sensing technologies and components may be employed in accordance with the teachings presented herein with regard to tissue fluid volume monitoring. It will be understood that other technologies and components may be used to monitor tissue fluid volume. For example, the concentration of an electrolyte, such as sodium, potassium, or calcium may be measured in a tissue using an ion selective electrode, with concentrations being higher with lower tissue fluid volume. By way of further example, a pressure sensor may be placed in the tissue to measure extension or contraction of tissue as fluid volume changes, stress and strain sensors may be used to measure modulus or stress-strain curves for tissue and may be used to correlate to different tissue fluid volumes, stress relaxation or creep profiles of tissue may be measured and correlated with different fluid volumes, etc. Another example of indirect tissue fluid monitoring is a measure of lung noise, which tends to be greater during fluid overload due to impedance of air flow.

Referring again to FIG. 8, sensor 220 may be a flow sensor, a gravimetric sensor, or any other suitable sensor capable of monitoring fluid volume or an indicator thereof. One or more of such sensors 220 may be employed to assist in determining how much fluid is removed from blood during a blood fluid removal session. Other suitable ways to determine fluid volume include utilizing a metering pump or utilizing a pressure sensor and knowing tubing diameter, calculating the volume.

While depicted in FIG. 8 as being separate, it will be understood that one or more of sensors 200, 210, 220, or components thereof, may be housed within a single housing, such as a housing containing sensor electronics or a housing of the blood fluid removal device.

Referring now to FIGS. 12-16 some representative methods that may be employed herein with regard to monitoring blood fluid volume and tissue fluid volume are presented as flow diagrams. It will be understood that the various flow diagrams are depicted to highlight certain pertinent aspects of the methods described herein and that even though they are presented separately in distinct flow diagrams, steps of the methods depicted in one flow diagram may be readily interchangeable or added to steps presented in another flow diagram.

Figure 12:
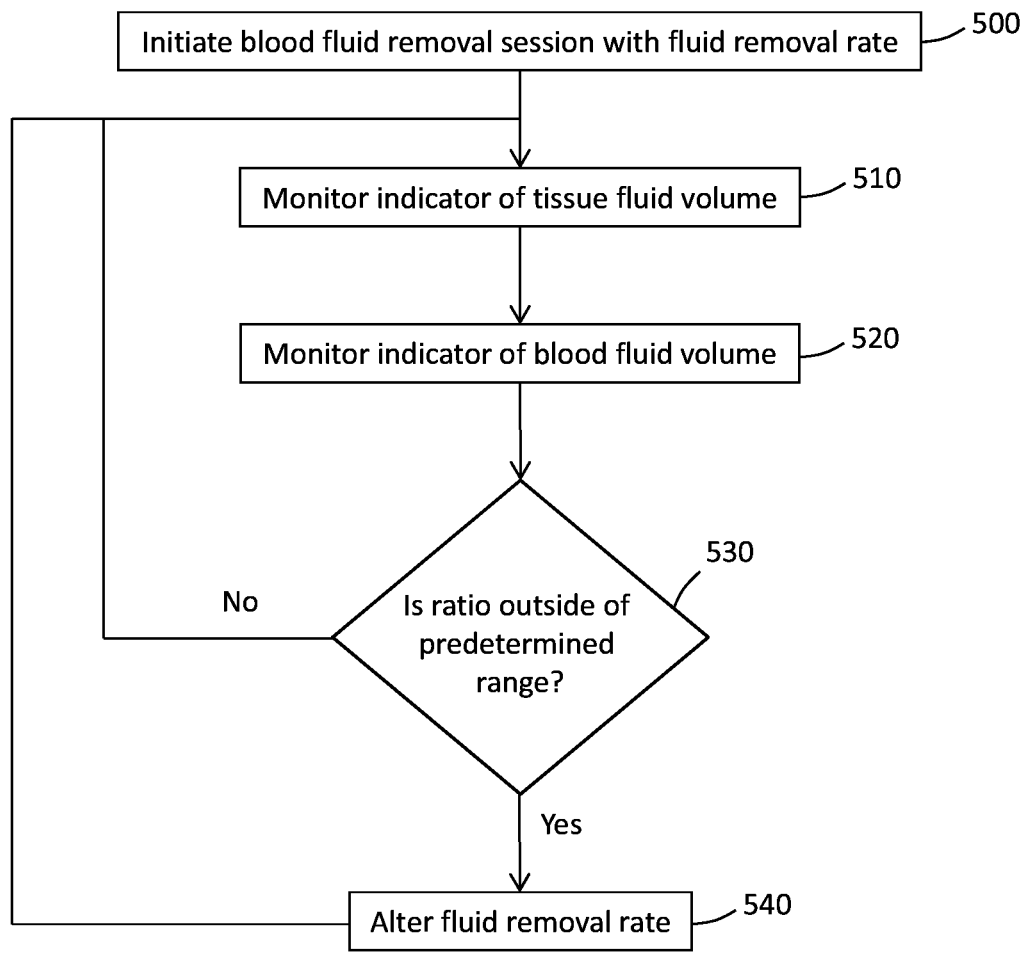
FIGS. 12-16 are flow diagrams depicting overviews of methods in accordance with various embodiments described herein.

In the embodiment depicted in FIG. 12, a blood fluid removal session is initiated (500) and indicators of tissue fluid volume (510) and blood fluid volume (520) are monitored. Of course, the blood fluid removal session may be essentially continuous, particularly with implantable blood fluid removal devices. Regardless of whether the blood fluid removal session lasts for a defined period of time or indefinitely, the ratio of blood fluid volume to tissue fluid volume is compared, and a determination as to whether the ratio is outside of a predetermined acceptable range is made (520). If the ratio is determined to not be outside the predetermined range, the blood fluid removal session continues with the previously set parameters with regard to fluid removal from the blood. If the ratio is determined to be outside the predetermined range, then rate of fluid removal from the blood is altered (540).

For example, if the ratio of the tissue fluid volume to blood fluid volume is above a predetermined threshold, the rate of fluid removal may be decreased. That is, if too much fluid is taken out of the blood or if fluid is removed at a rate faster than the rate at which fluid from the tissue may fill the blood volume, the ratio of tissue fluid volume to blood fluid volume will increase. If the ratio increases to an extent beyond a predetermined acceptable level, the rate of fluid removal can be decreased to allow more time for fluid from the tissue to flow into the blood and bring the fluids in the blood compartment and tissue compartment into appropriate balance and avoiding an undesired fluid imbalance that can have negative consequences on patient health.

In contrast, if the ratio of tissue fluid volume to blood fluid volume is below a predetermined threshold, the rate of fluid removal from the blood may be increased. For example, for purposes of efficiency it may be desirable to keep a slight, but safe fluid imbalance between the blood compartment and the tissue compartment to drive out excess fluid at a safe and efficient rate. While a low ratio of tissue fluid volume to blood fluid volume may not result in a health risk to the patient (provided that a sufficient volume of fluid is eventually removed), the time in which a patient undergoes a blood fluid removal process may be unnecessarily extended. Thus, by monitoring tissue fluid volume and blood fluid volume during a blood fluid removal session, the rate of fluid removal can be finely controlled based on the monitored indicators to enhance patient safety and to enhance efficiency of the blood fluid removal process.

A ratio of tissue fluid volume to blood fluid volume being too low may also be indicative of too much replacement fluid being added to blood prior to returning the blood to the patient. Accordingly, the rate at which replacement fluid is added may be decreased (which effectively increases the rate of fluid removal for purposes of the present disclosure).

An appropriate range of tissue fluid volume to blood fluid volume may be determined in any suitable manner. For example, the ratio at the patient's dry weight may be defined as the reference. In general, blood is about 7% of body weight and total tissue fluid is about 60% of the body weight (including blood, extracellular and intracellular fluid). Thus, the typical tissue to blood fluid volume ratio of a healthy individual is 53/7, or about 7.6 (e.g., in the range of 6 to 9). This can be used as a starting point for an appropriate ratio of tissue fluid volume to blood fluid volume to be achieved. Alternatively or in addition, the reference ratio may be obtained through a learning process over the course of therapy and may be patient-dependent. The pattern of change of the tissue to blood volume ratio (or indicators thereof) may be optimized through the learning process. As an optimized pattern is learned, it may be used to guide personalized therapy to achieve better outcomes on a patient-by-patient basis.

In some embodiments, a learning algorithm or evolving algorithm that looks at the rate of change of both blood and tissue is used. The difference in rate of change may be used to determine the time constant of the fluid exchange between the tissue and blood compartments. This information can then be used to establish a target on hematocrit (or other indicator of blood fluid volume) for a final state, while taking into consideration the slower transfer between tissue and blood compartments. This could be used to dynamically adjust the fluid removal rate. Limits may be established by patient or clinician input. The initial calibration may be learned or may utilize other information such as weight or other external lab input.

Figure 13:
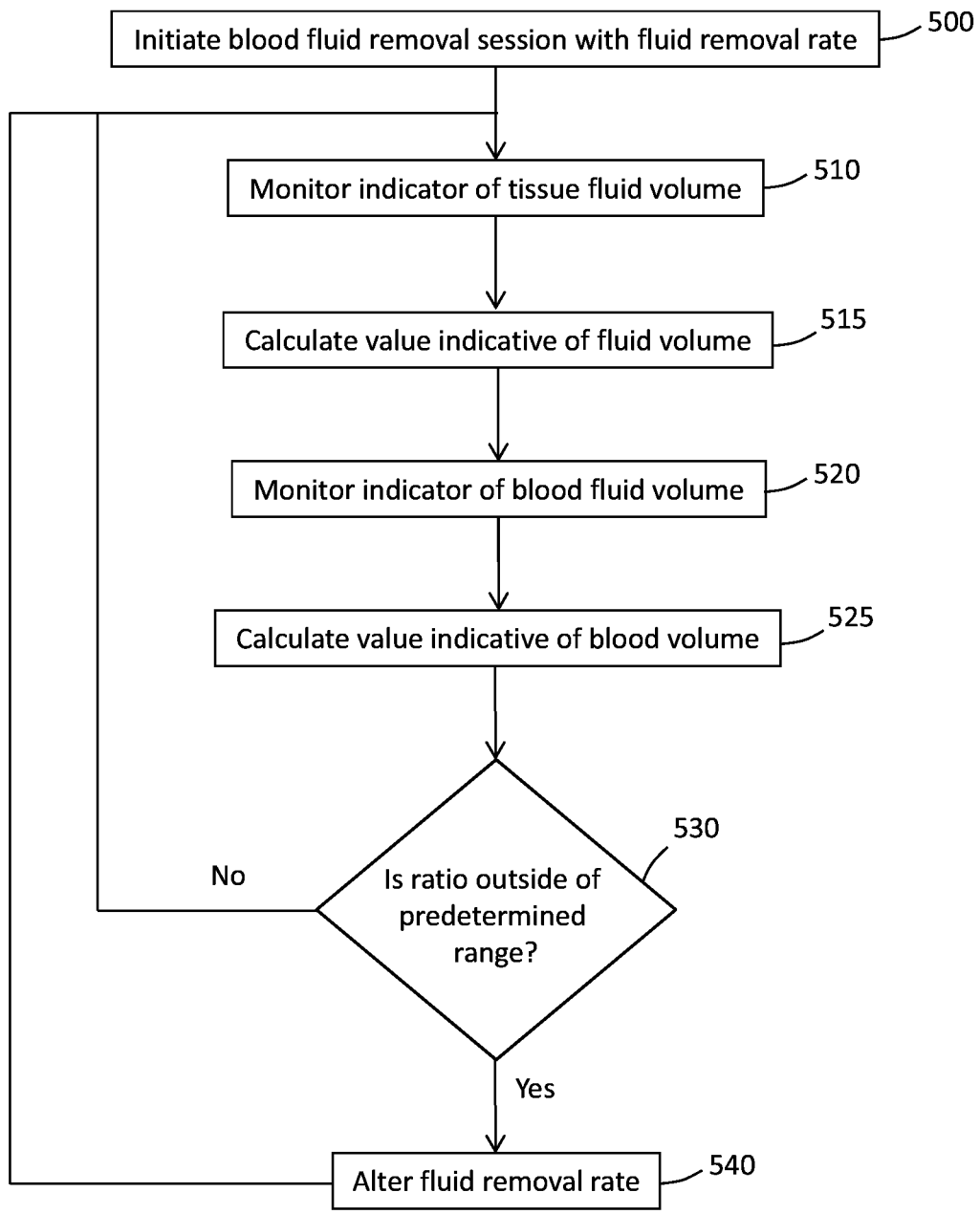

Referring now to FIG. 13, a method similar to that depicted in FIG. 12 is shown. In FIG. 13, the method includes calculating a value indicative of tissue fluid volume (515) based on the monitored indicator (510) and calculating a value indicative of blood volume (525) based on the monitored indicator (520). The ratio of tissue fluid volume to blood fluid volume may be determined based on these calculated values (530) rather than on the values obtained with regard to the monitored indicators themselves as depicted in FIG. 12. In either case, the outcome is essentially the same, provided that differences in the way indicators of tissue and blood fluid volume can predict volume are accounted for.

For example, if tissue fluid volume is determined by impedance, an increase in tissue fluid volume would result in an increase in impedance. However, if hematocrit levels were used to determine blood fluid volume, an increase in blood fluid volume would result in a decrease in hematocrit. Accordingly, if the determination regarding the ratios in the embodiment in FIG. 12 took into account that a increase in hematocrit indicates an decrease in blood fluid volume, the end result would be essentially the same as would be obtained in the method of FIG. 13. Put another way, if it was understood and accounted for that the ratio of impedance to the hematocrit changes differently from the ratio of tissue fluid volume to blood fluid volume, the methods of FIG. 12 and FIG. 13 will produce similar results with regard to altering the rate at which fluid is removed from the blood.

Figure 14:
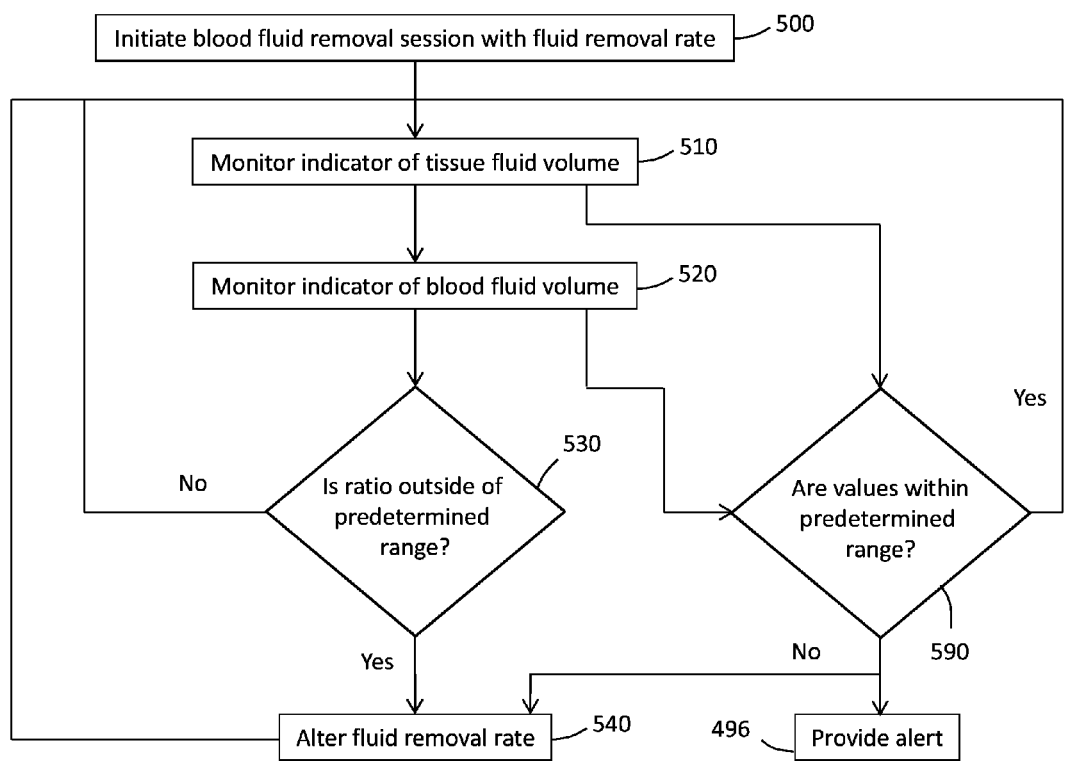

As depicted in FIG. 14, the methods described herein may, in some embodiments, use the monitored indicators of tissue fluid volume (510) or blood fluid volume (520) alone, in addition to the ratio of such values, for purposes of patient safety. As depicted in FIG. 14, it may be determined whether the individually monitored indicator of tissue fluid volume or blood fluid volume are within predetermined acceptable ranges (590). For example, if tissue fluid volume or blood fluid gets unacceptably low (even though the ratio may be within acceptable ranges) or too high, the rate of fluid removal from blood may be altered (540). By way of example, if a value of the indicator of tissue fluid volume is indicative of a near dry weight volume, the rate of fluid removal from blood may be reduced to allow a proper ratio of tissue fluid volume to blood fluid volume to be achieved prior to reaching the dry weight fluid volume. Thus in some embodiments, the threshold for determining whether a value of the monitored indicator of blood of tissue fluid volume is outside of a predetermined range may change based on the ratio of tissue to blood fluid volume. For example, if the ratio of tissue to blood fluid volume is high (indicating a rapid removal of fluid from blood), then the lower threshold for tissue fluid volume (e.g., nearing dry weight) may be higher than if the ratio of tissue to blood fluid volume was low (suggesting less rapid removal of fluid from blood) to avoid overshooting the dry weigh tissue fluid volume.

As also depicted in FIG. 14, an alert such as an audio or visual alarm may be provided (496) to alert the patient or a healthcare provider that a potentially dangerous patient health situation exists with regard to too high or too low fluid volume in the tissue or blood.

Figure 15:
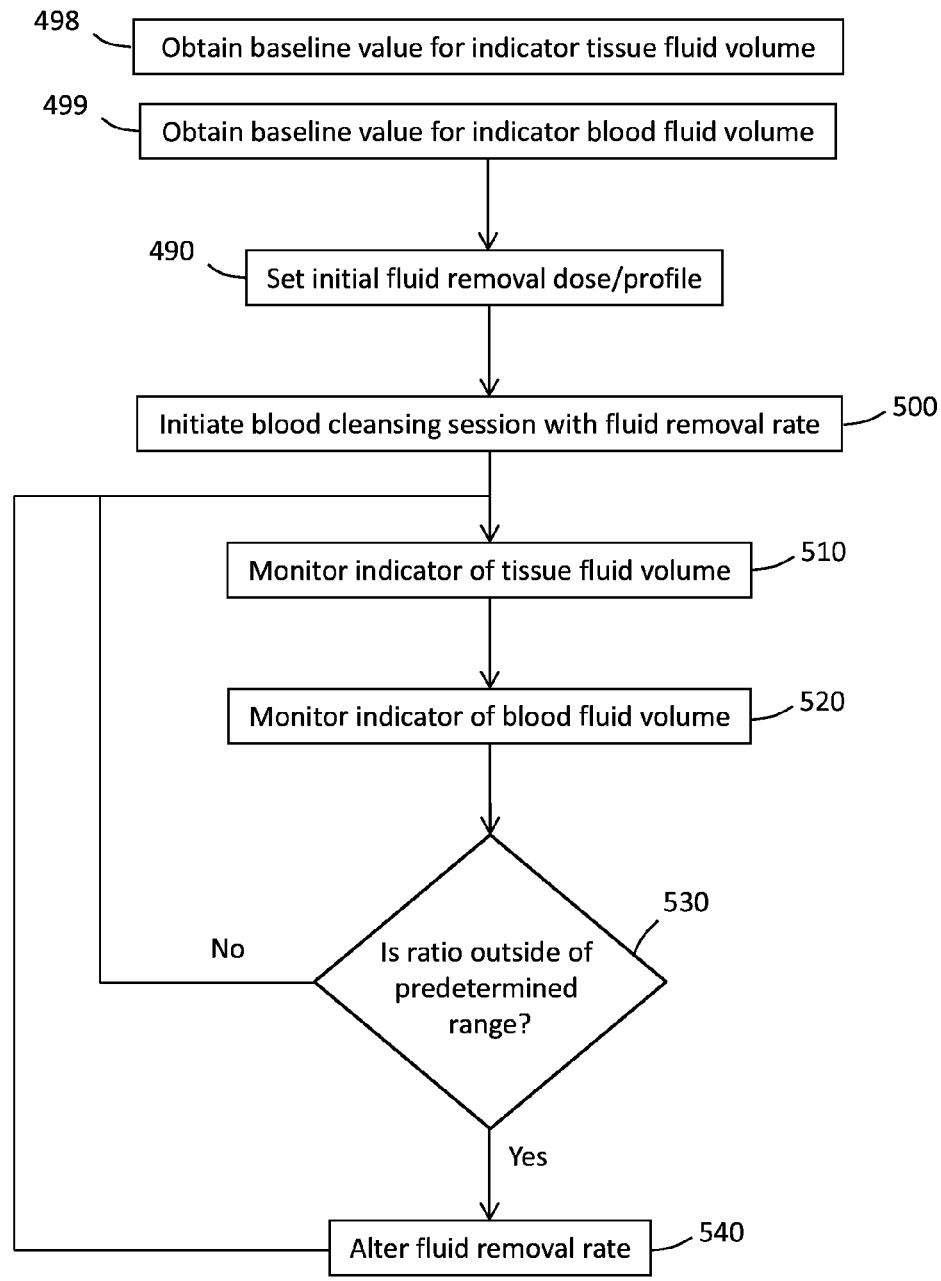

Referring now to FIG. 15, a method similar to that depicted in FIG. 12 is shown. The method in FIG. 15 includes obtaining a baseline value for an indicator of tissue fluid volume (498) or obtaining a baseline value for an indicator of blood fluid volume (499) prior to initiating a blood fluid removal session (500). One or both of the baseline values may be used to determine the initial dose or prescription for fluid removal for the blood fluid removal session (490). The rate of fluid removal from the blood may be adjusted (540) during the blood fluid removal session based on monitoring (510, 520) that occurs during the session.

Figure 16:
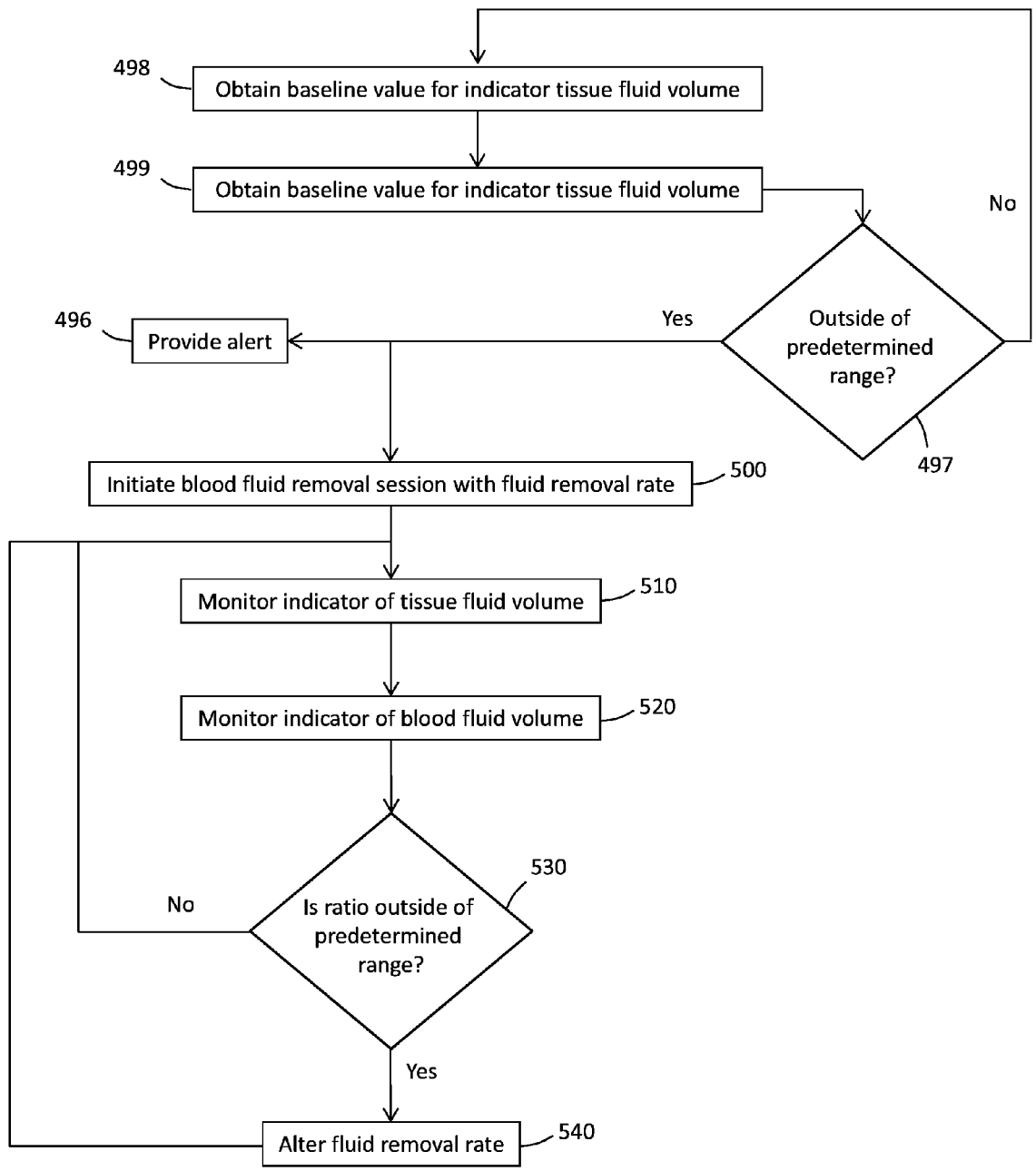

Referring now to FIG. 16, a method similar to that depicted in FIG. 12 is shown. The method in FIG. 16, like the method depicted in FIG. 15, includes obtaining a baseline value for an indicator of tissue fluid volume (498) or obtaining a baseline value for an indicator of blood fluid volume (499) prior to initiating a blood fluid removal session (500). If the values are determined to be outside of predetermined acceptable ranges (497), a blood fluid removal session may be initiated (500). Such a method may be advantageously employed in situations where the blood fluid removal device and monitoring sensors are implanted or continuously operating or available to operate, as a blood fluid removal session may be automatically initiated. Alternatively or in addition, the method depicted in FIG. 16 may include providing an alert (496) to the patient or healthcare provider indicating that a blood fluid removal session is advised.

Hypotension is the main complication during dialysis (25-60%). With the methods described herein, which may include real-time blood pressure sensors or other blood volume sensors, imminent blood pressure changes or levels may be predicted, e.g. on a feed-forward basis. Accordingly, the rate of fluid removal may be adjusted based on data collected during the fluid removal session to avoid a hypotension situation, as opposed to current standard of care where one starts to adjust the fluid removal rates only when one sees the problems. Dry weight and optimized tissue to blood fluid ratios learned, e.g. as described above, from the therapy course of a patient may help this prediction process to be effective and practical. If necessary or desired, replacement fluid, dialysate or removed fluid may be introduce into blood before it is returned to the patient to avoid, mitigate or correct a hypotensive event; e.g., as discussed above with regard to FIGS. 1-4.

The methods described above, such as the methods described and depicted with regard to FIGS. 12-16, may be applied with any suitable blood fluid removal device or system, such as those depicted and described with regard to FIGS. 1-4 above. In addition, any suitable sensor, sensor configuration, placement or orientation, may be employed, such as those depicted and described above with regard to FIGS. 8-11 in carrying out the methods described herein. In the drawings provided in FIGS. 17-20 below, various particular configurations of blood fluid removal devices 100 or systems and sensors 200, 210, 220 are shown. However, it will be understood that the specific devices 100 and the interaction of sensors 200, 210, 220 are shown for purposes of illustration and that other devices and configurations may be employed.

Figure 17:
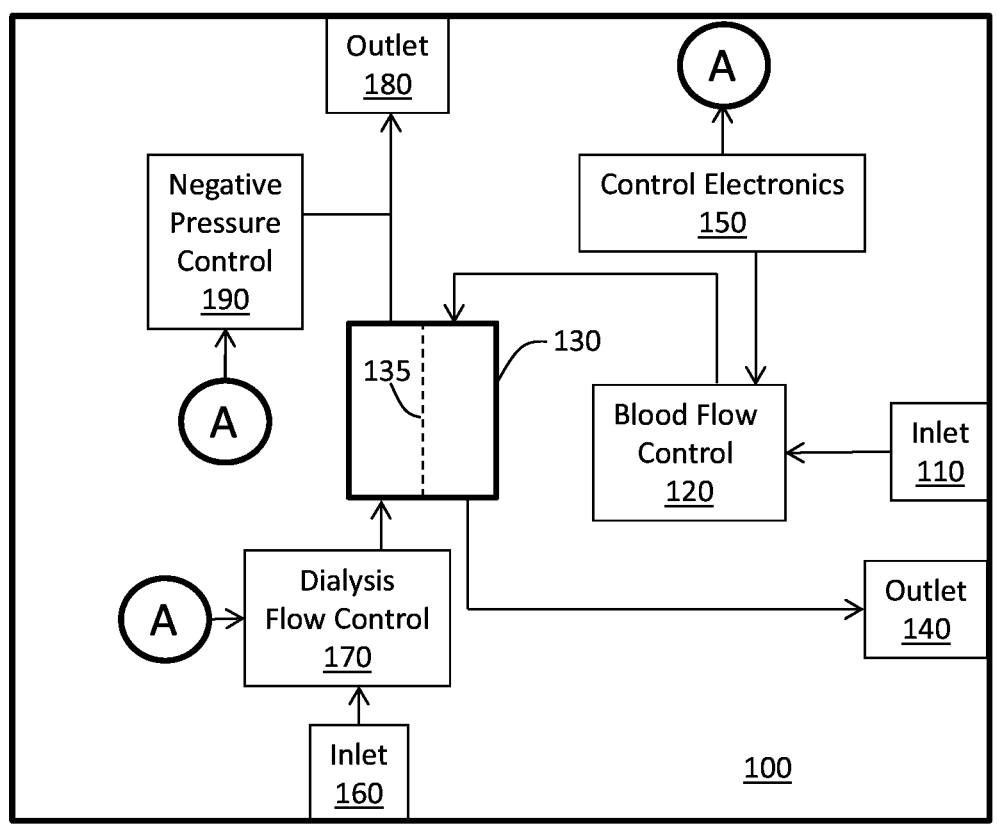
FIGS. 17-18 are schematic block diagrams of selected components of blood fluid removal devices or systems that may be employed in accordance with various embodiments presented herein.

Referring now to FIG. 17, a schematic block diagram of selected components of a blood fluid removal device 100 is shown. In the depicted embodiment, the device has in inlet 110 for receiving blood from a patient, a blood flow control element 120 in communication with the inlet 110 and configured to control the rate at which blood flows through medium 130 for removing fluid and contaminates from the blood. The device also includes an outlet 140 in communication with the medium 130 for returning blood to the patient. In the depicted embodiment, the medium 130 includes a semipermeable membrane 135, such as a hemodialysis or hemodiafiltration filter. The membrane separates a blood flow compartment from a dialysis flow compartment of the medium 130. The device 100 has an inlet 160 for receiving fresh dialysate. Inlet 160 is in communication with a dialysis flow control element 170 for controlling the rate at which dialysis is introduced into the dialysis flow compartment of the medium 130. The device also has an outlet 180 in communication with the medium 130 for diverting used dialysate and fluid removed from the blood out of the device. In the depicted embodiment, the device also includes a negative pressure control element 190 in communication with the dialysate compartment of the medium component 130, as needed or desired. The device 100 also includes control electronics 150, which may include a processor, etc., operably coupled to, and configured to control, the blood flow control element 120, the dialysis flow control element 170, and the negative pressure control element 190.

Based on information received from sensors that monitor blood fluid volume or tissue fluid volume, the control electronics 150 can control one or more of the blood flow control element 120, the dialysis flow control element 170, and the negative pressure control element 190 to adjust the rate at which fluid is removed from the blood of the patient. For example, altering the flow rate of the blood (via the blood flow control element 120) through the medium component 130 may alter fluid clearance across the membrane. Altering flow of dialysate (via dialysis flow control element 170) through the medium component 130 may similarly alter fluid clearance across the membrane. Negative pressure (via negative pressure control element 190) may be applied on the dialysate compartment side of the membrane 135 and may result in greater fluid clearance across the membrane due to convective forces. It will be understood that a device 100 need not have all of the controllable elements (120, 170, 190) depicted in FIG. 17 to effectively control rate of fluid removal from blood based on data from sensors that monitor indicators of tissue fluid volume and blood fluid volume.

Any suitable blood flow control elements 120 may be used to control flow of blood through the membrane component 130. For example, a variable or adjustable rate pump may be employed. Alternatively or in addition, a series of electronically controllable valves in communication flow paths having differing resistance to flow may be employed (in such cases the flow restrictors would preferably be downstream of the medium component 130). Dialysis flow control element 170 may contain similar components or be similarly configured to blood flow control element 120. The negative pressure control element 120 may include a pump or the like.

Figure 18:
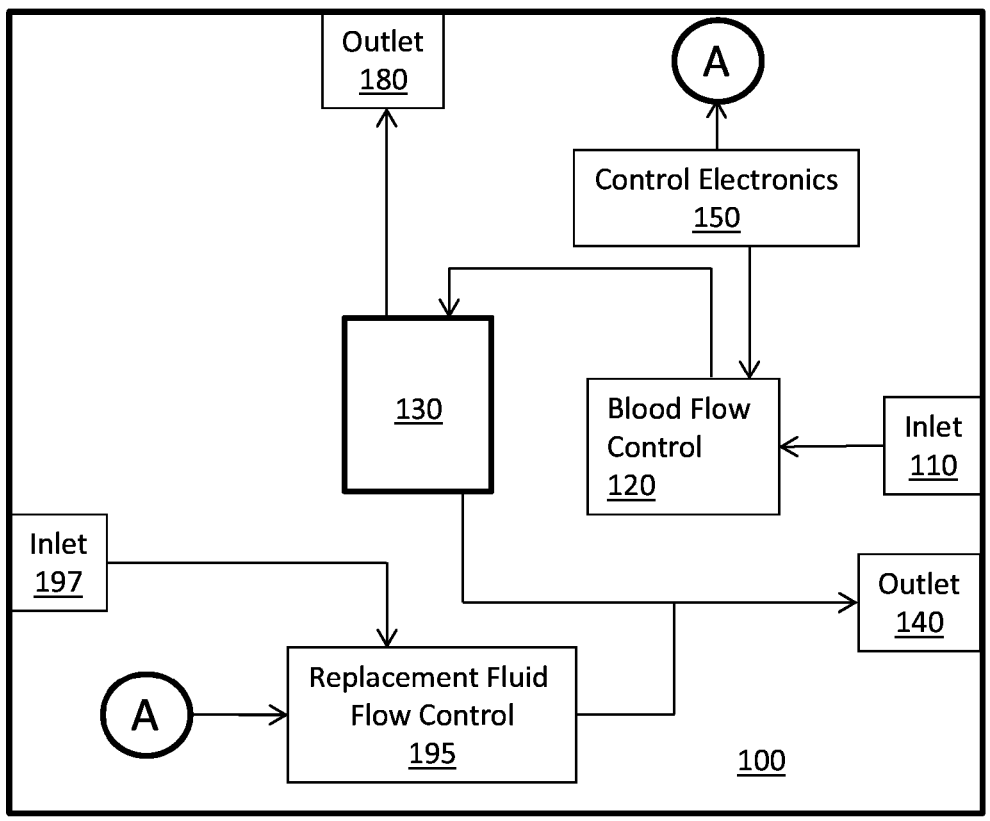
Figure 19:
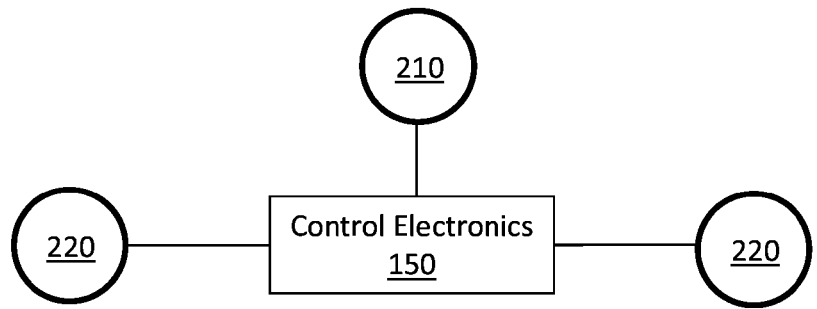
FIG. 19 is a schematic block diagram showing interactions between various sensors and control electronics.

Referring now to FIG. 18, in which components that are numbered the same as in FIG. 17 refer to the same or similar components, the device 100 may include a fluid pathway for adding replacement fluid to blood before it is returned to the patient. The device 100 includes an inlet 197 for receiving the replacement fluid and a replacement fluid flow control element 195 in communication with the inlet and configured to control the rate at which the replacement fluid is added to the blood. The control electronics 150 are operable coupled to the replacement fluid flow control element 195 and are configured to control the rate at which replacement fluid flow control element 195 adds fluid to the blood based on data received from sensors that monitor blood fluid volume or tissue fluid volume. By controlling the rate at which fluid is introduced into blood, the rate of effective fluid removal from the blood is controlled.

Any suitable replacement fluid flow control element 195 may be used to control flow of replacement fluid into the blood before being returned to the patient. Replacement fluid flow control element 195 may contain similar components or be similarly configured to blood flow control element 120 as described above with regard to FIG. 18.

As discussed above and as shown in FIG. 19, one or more sensing devices 200, 210, 220 or sensing components may communicate with control electronics 150 of a blood fluid removal device 100 or system. The communication may be direct or indirect. That is, a detector and appropriate electronics, such as filters, analog-to-digital converters or the like, may be directly coupled to sensing electronics 150 of the device 100 via a lead. Alternatively, a sensing device may obtain monitored data and transmit the data to the sensing electronics 150 of the device. In any case, the sensing electronics are configured to control the rate of fluid removal from blood based on the sensed information, e.g. as described above.

In some embodiments, a computer readable medium contains instructions that cause the processor of control electronics to carry out the methods described above, e.g. the methods depicted and described above with regard to FIGS. 12-16. The computer readable medium may be non-transitory (e.g., stored in memory, etc.).

Figure 20:
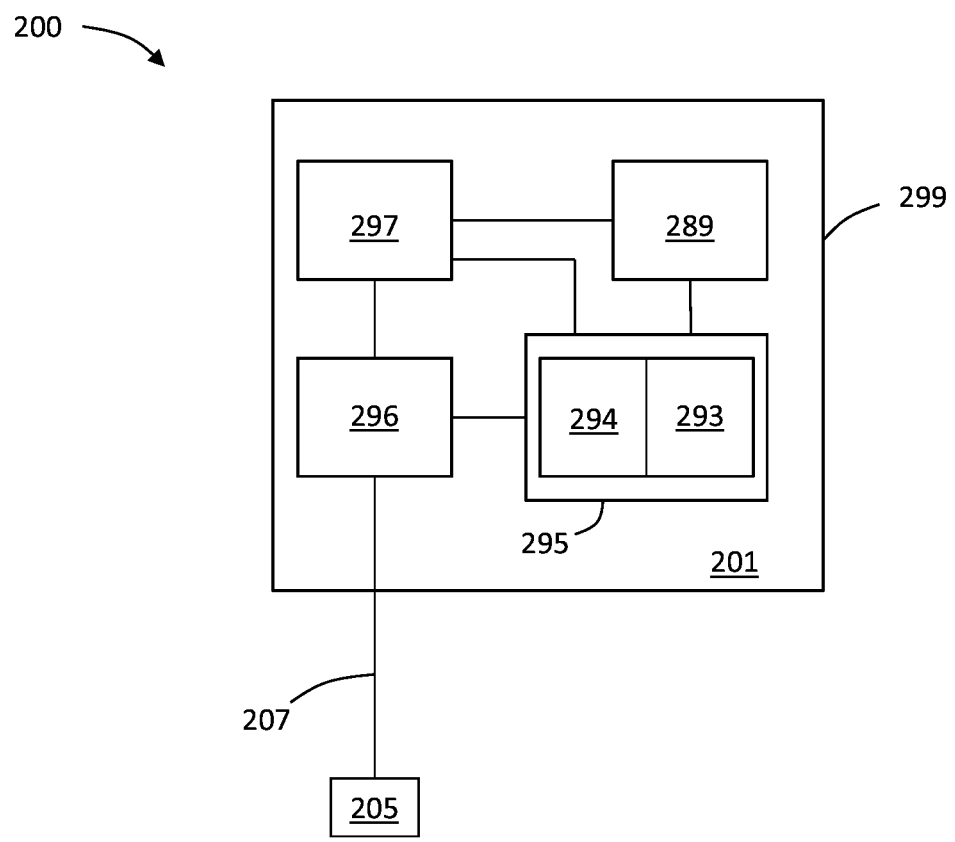
FIG. 20 is a schematic block diagram showing selected components of a sensor.

For purposes of illustration, a block diagram of a stand-alone sensing device 200 is shown in FIG. 20. The depicted sensing device is an impedance sensor, but the discussion with regard to this sensor is readily applicable to other types of sensors. The depicted sensor is implantable and has a hermetically sealed conductive housing 299 that serves as a counter electrode to electrode 205. Electrode 205 is operably coupled to impedance detecting and voltage generating circuitry 296 via lead 207 that enters housing via a feedthrough (not shown). Circuitry 296 is operably coupled to power source 297 and control electronics 295, which include a processor 294 and a memory 293 for storing sensed data and processor instructions. Control electronics are also operably coupled to power source 297, which may be a battery or the like, and to telemetry circuitry 289 for wirelessly communicating with a device external to the patent. In some embodiments, the telemetry circuitry allows the sensor device 200 to transmit data regarding a monitored indicator of fluid volume directly to a blood fluid removal device or system that is equipped with suitable telemetry circuitry (not shown in FIGS. 17-18).

Of course, a sensing device may communicate with one or more intermediary device before data is sent to the blood fluid removal device or system to use the data to control the rate of fluid removal from blood in accordance with the teachings presented herein.

Various aspects of methods, systems, devices, computer-readable media, etc. are described herein. A summary of some of the aspects described herein is presented below.

In a first aspect a method carried out by a blood fluid removal device is described. The method includes (i) initiating a blood fluid removal session of a patient; (ii) monitoring an indicator of tissue fluid volume of the patient, or a portion thereof, during the blood fluid removal session; (iii) monitoring an indicator of blood fluid volume of the patient during the blood fluid removal session; (iv) determining whether a ratio of the indicator of tissue fluid volume to indicator of blood fluid volume is outside of a predetermined range; and (iv) altering the rate of fluid removal during the blood fluid removal session if the ratio is determined to be outside of the predetermined range.

A second aspect is a method of the first aspect, wherein the predetermined range is based on measurements of the indicator of tissue fluid volume and the indicator of blood fluid volume obtained prior to initiating the blood fluid removal session.

A third aspect is a method of the first or second aspect, wherein if the ratio the indicator of tissue fluid volume to the indicator of blood fluid volume is outside the predetermined range and is indicative of exceeding a threshold of tissue fluid volume to blood fluid volume, then the rate of fluid removal is decreased.

A fourth aspect is a method of any of aspects 1-3, wherein if the ratio the indicator of tissue fluid volume to the indicator of blood fluid volume is outside the predetermined range and is indicative of a falling below a threshold of tissue fluid volume to blood fluid volume, then the rate of fluid removal is increased.

A fifth aspect is a method of any of aspects 1-4, further comprising monitoring the indicator of tissue fluid volume of the patient prior to initiating the blood fluid removal session or monitoring the indicator of blood fluid volume of the patient prior to initiating the blood fluid removal session; and setting an initial fluid volume removal prescription for the blood fluid removal session based on the indicator of tissue fluid volume monitored prior to initiating the blood fluid removal session or the indicator of blood fluid volume monitored prior to initiating the blood fluid removal session.

A sixth aspect is a method of claim 5, wherein monitoring the indicator of tissue fluid volume of the patient prior to initiating the blood fluid removal session or monitoring the indicator of blood fluid volume of the patient prior to initiating the blood fluid removal session comprises chronically monitoring the indicator of tissue fluid volume.

A seventh aspect is a method of aspect 6, further comprising (i) determining whether the indicator of tissue fluid volume or the indicator of blood fluid volume monitored prior to initiating the blood fluid removal session crosses a predetermined threshold value, and (ii) scheduling the blood fluid removal session or providing an alert if the indicator crosses the threshold value.

An eighth aspect is a method of any of aspects 1-7, further comprising: (i) determining whether the indicator of tissue fluid volume is outside of a predetermined range or determining whether the indicator of blood fluid volume is outside of a predetermined range; and (ii) altering the rate of fluid removal if the indicator of tissue fluid volume is determined to be outside of a predetermined range or if the indicator of blood fluid volume is determined to be outside of a predetermined range.

A ninth aspect is a method of aspect 8, wherein the predetermined range of the indicator of tissue fluid volume or the predetermined range of blood fluid volume is determined based on the ratio of the indicator of tissue fluid volume to blood fluid volume.

A tenth aspect is a method of aspect 8 or 9, wherein a determination as to whether the indicator of tissue fluid volume is outside of a predetermined range is made.

An eleventh aspect is a method of any of aspects 1-10, wherein the indicator of tissue fluid volume is impedance of flow of electricity through tissue of the patient.

A twelfth aspect is a method of claim 11, wherein the impedance is measured between two electrodes placed in contact with the patient's skin.

A thirteenth aspect is a method of any of aspects 1-12, wherein monitoring the indicator of blood fluid volume comprises measuring a hematocrit level, or an indicator thereof.

A fourteenth aspect is a method of aspect 13, wherein measuring the hematocrit level or the indicator thereof comprises measuring oxygenated hemoglobin concentration.

A fifteenth aspect is a method comprising: (i) initiating a blood fluid removal session of a patient; (ii) monitoring an indicator of tissue fluid volume of the patient, or a portion thereof, during the blood fluid removal session; (iii) calculating a value indicative of tissue fluid volume based on the monitored indicator of tissue fluid volume; (iv) monitoring an indicator of blood fluid volume of the patient during the blood fluid removal session; (v) calculating a value indicative of blood fluid volume based on the monitored indicator of blood fluid volume; (vi) determining whether a ratio of the value indicative of tissue fluid volume to the value indicative of blood fluid volume is outside of a predetermined range; and (vii) altering the rate of fluid removal during the blood fluid removal session if the ratio is determined to be outside of the predetermined range.

A sixteenth aspect is a system comprising: (a) a blood fluid removal device comprising (i) an inlet for receiving blood from a patient, (ii) an first outlet for returning blood from the patient, (iii) a medium for removing fluid and contaminants from the blood, the medium being positioned between the inlet and the first outlet, (iv) a fluid rate removal controller; and (v) a second outlet for flow of the removed fluid and contaminants; (b) a first sensor for monitoring an indicator of tissue fluid volume; (c) a second sensor for monitoring an indicator of blood fluid volume; (d) control electronics in operable communication with the sensor for monitoring an indicator of tissue fluid volume, the sensor for monitoring an indicator of blood fluid volume; and the fluid rate removal controller, wherein the control electronics are configured to adjust the rate at which fluid is removed based on data obtained from the first sensor and the second sensor.

A seventeenth aspect is a system of aspect 16, further comprising a computer readable medium, wherein the computer readable medium comprises instructions that cause the control electronics to adjust the rate at which fluid is removed based on data obtained from the first sensor and the second sensor.

An eighteenth aspect is a system of aspect 16, wherein the computer readable medium comprises instructions that cause the control electronics to (i) calculate a ratio of the indicator of tissue fluid volume to the indicator of blood fluid volume based on data obtained from the first and second sensors, respectively; (ii) determine whether the calculated ratio is outside of a predetermined range; and (iii) alter the rate of fluid removal if the ratio is determined to be outside of the predetermined range.

A nineteenth aspect is a system of aspect 16, wherein the computer readable medium comprises instructions that cause the control electronics to (i) calculate a value indicative of tissue fluid volume based data obtained from the first sensor; (ii) calculate a value indicative of blood fluid volume based on data obtained from the second sensor; (iii) determine whether a ratio of the value indicative of tissue fluid volume to the value indicative of blood fluid volume is outside of a predetermined range; and (iv) alter the rate of fluid removal if the ratio is determined to be outside of the predetermined range.

A twentieth aspect is a system of any of aspects 16-19, wherein the fluid rate removal controller comprises one or more of a blood flow control component, a negative pressure control component, a dialysis flow control component, and a fresh fluid flow control component.

A twenty-first aspect is a system of any of aspects 16-20, wherein the medium for removal of fluid and contaminants from the blood comprises a filtration membrane.

A twenty-third aspect is a system of any of aspects 16-21, wherein one or more components of the first sensor, the second sensor and the control electronics are housed within the blood fluid removal device.

Thus, systems, devices and methods for FLUID VOLUME MONITORING FOR PATIENTS WITH RENAL DISEASE are described. Those skilled in the art will recognize that the preferred embodiments described herein may be altered or amended without departing from the true spirit and scope of the disclosure, as defined in the accompanying claims.

In the claims that follow, the designators "first", "second", "third" and the like are used for purposes of distinguishing between elements and not for purposes of enumerating the elements or for defining a sequence of the elements. For example, a "third" sensor does not necessarily imply that there are three sensors but rather that the "third" sensor is distinct from the "first" sensor. By way of further example, a "third" sensor does not necessarily come later in time than a "first" sensor.

We claim:

1. A method, comprising:
    initiating a blood fluid removal session of a patient with an initial blood fluid removal rate;
    monitoring an indicator of tissue fluid volume of the patient during the blood fluid removal session;
    monitoring an indicator of blood fluid volume of the patient during the blood fluid removal session;
    determining a first indicator of tissue fluid volume and a first indicator of blood fluid volume;
    acquiring a first set of data regarding the physiological health of the patient;
    altering the rate of blood fluid removal to a second blood fluid removal rate;
    determining a second indicator of tissue fluid volume and a second indicator of blood fluid volume;
    acquiring a second set of data regarding the physiological health of the patient;
    determining a preferable outcome measure based on the first and second sets of physiological data; and
    altering the rate of blood fluid removal so that an indicator of tissue fluid volume and an indicator of blood fluid volume are within a pre-determined range of the preferable outcome measure.

2. The method of claim 1, wherein the outcome measure is any one of a degree of hypotension, a deviation from dry weight, or combinations thereof.

3. The method of claim 1, further comprising determining a ratio of the indicator of blood fluid volume to the indicator of tissue fluid volume; and
    altering the rate of blood fluid removal so that the ratio of the indicator of tissue fluid volume to the indicator of blood fluid volume is within a pre-determined range of the preferable outcome measure.

4. The method of claim 1, further comprising:
    determining whether the indicator of tissue fluid volume or the indicator of blood fluid volume crosses a predetermined threshold during the blood fluid removal session.

5. The method of claim 4, wherein if the indicator of blood fluid volume or the indicator of tissue fluid volume crosses the predetermined threshold, altering the rate of blood fluid removal.

6. The method of claim 1, wherein the indicator of tissue fluid volume is tissue impedance.

7. The method of claim 1, wherein the indicator of blood fluid volume is a hematocrit level, or an indicator thereof.

8. The method of claim 7, wherein measuring the hematocrit level comprises measuring oxygenated hemoglobin concentration.

9. The method of claim 1, wherein one or both of the indicator of tissue fluid volume and the indicator of blood fluid volume are measured with one or more implantable sensors.

10. The method of claim 1, wherein the blood fluid removal session is carried out with an implantable blood fluid removal device.

11. The method of claim 1, wherein the blood fluid removal session is carried out with a wearable blood fluid removal device.

12. The method of claim 1, wherein if the indicator of tissue fluid volume or the indicator of blood fluid volume is outside of a pre-determined range, an alert is provided.

13. A method carried out by a blood fluid removal system comprising:
    initiating a blood fluid removal session of a patient;
    monitoring an indicator of tissue fluid volume of the patient, or a portion thereof, during the blood fluid removal session;
    monitoring an indicator of blood fluid volume of the patient during the blood fluid removal session;
    determining whether the indicator of tissue fluid volume and the indicator of blood fluid volume are outside of a predetermined range; and
    altering the rate that replacement fluid is added to the blood if the indicator of tissue fluid volume or the indicator of blood volume is determined to be outside of the predetermined range.

14. The method of claim 13, wherein the replacement fluid is added to the blood prior to fluid being removed from the blood.

15. The method of claim 13, wherein the replacement fluid is added to the blood after fluid being removed from the blood.

16. The method of claim 13, further comprising obtaining a ratio of the indicator of tissue fluid volume to the indicator of blood fluid volume;

determining whether the ratio of the indicator of tissue fluid volume to the indicator of blood fluid volume is outside of a predetermined range; and altering the rate that the replacement fluid is added to the blood if the ratio of the indicator of tissue fluid volume to the indicator of blood fluid volume is outside of the predetermined range.

17. The method of claim 13, wherein if the indicator of tissue fluid volume or the indicator of blood fluid volume is outside of a pre-determined range, an alert is provided.

18. The method of claim 13, further comprising altering a rate of blood fluid removal if the indicator of tissue fluid volume or the indicator of blood volume is determined to be outside of the predetermined range.

19. A system, comprising:
a blood fluid removal device comprising
(i) an inlet for receiving blood from a patient,
(ii) a first outlet for returning blood from the patient,
(iii) a medium for removing fluid and contaminants from the blood, the medium being positioned between the inlet and the first outlet,
(iv) a fluid rate removal controller; and
(v) a second outlet for flow of the removed fluid and contaminants;
a first sensor for monitoring an indicator of tissue fluid volume;
a second sensor for monitoring an indicator of blood fluid volume;
control electronics in operable communication with the sensor for monitoring an indicator of tissue fluid volume, the sensor for monitoring an indicator of blood fluid volume; and the fluid rate removal controller,
wherein the control electronics are configured to carry out the method of claim 1.

20. The system of claim 19, wherein the medium for removal of fluid and contaminants from the blood comprises a filtration membrane.

21. The system of claim 19, wherein one or more components of the first sensor, the second sensor and the control electronics are housed within the blood fluid removal device.

* * * * *